US009622747B2

(12) United States Patent
Fanelli et al.

(10) Patent No.: US 9,622,747 B2
(45) Date of Patent: *Apr. 18, 2017

(54) SURGICAL INSTRUMENT END EFFECTOR ARTICULATION DRIVE WITH PINION AND OPPOSING RACKS

(71) Applicant: ETHICON ENDO-SURGERY, INC., Cincinnati, OH (US)

(72) Inventors: Nicholas Fanelli, Morrow, OH (US); Jeffrey C. Gagel, Loveland, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/879,301

(22) Filed: Oct. 9, 2015

(65) Prior Publication Data

US 2016/0030043 A1    Feb. 4, 2016

Related U.S. Application Data

(63) Continuation of application No. 13/780,067, filed on Feb. 28, 2013, now Pat. No. 9,186,142.

(51) Int. Cl.
*A61B 17/00*   (2006.01)
*A61B 17/072*  (2006.01)
*A61B 17/29*   (2006.01)

(52) U.S. Cl.
CPC ............... *A61B 17/07207* (2013.01); *A61B 2017/00318* (2013.01); *A61B 2017/00367* (2013.01);

(Continued)

(58) Field of Classification Search
CPC ......... A61B 17/00; A61B 17/28; A61B 17/29; A61B 17/32

(Continued)

(56) References Cited

U.S. PATENT DOCUMENTS

| 4,805,823 A | 2/1989 | Rothfuss |
| 5,307,976 A | 5/1994 | Olson et al. |

(Continued)

FOREIGN PATENT DOCUMENTS

| EP | 1 749 485 | 2/2007 |
| EP | 1 915 953 | 4/2008 |
| EP | 2 042 107 | 4/2009 |

OTHER PUBLICATIONS

European Search Report and Written Opinion dated May 27, 2014 for Application No. EP 14157346.9, 7 pgs.

(Continued)

*Primary Examiner* — Ahmed Farah
(74) *Attorney, Agent, or Firm* — Frost Brown Todd LLC

(57) ABSTRACT

An apparatus includes a body and a shaft assembly. The shaft assembly is in communication with the body and includes an end effector, first cam gear, second cam gear, and a lock bar. The end effector has an articulation joint. The first cam gear is rotatably positioned within the shaft assembly. The second cam gear is in communication with the end effector at the articulation joint. The lock bar is distally biased to lock against the second cam gear. The first cam gear is rotatable through a first range of motion to unlock the lock bar relative to the second cam gear. The first cam gear is rotatable through a second range of motion to rotate the end effector at the articulation joint.

14 Claims, 25 Drawing Sheets

(52) U.S. Cl.
CPC ............... *A61B 2017/00389* (2013.01); *A61B 2017/2927* (2013.01); *A61B 2017/2946* (2013.01)

(58) Field of Classification Search
USPC ......... 606/1, 130; 227/175.1, 175.2; 492/15, 492/16; 74/640, 321–325
See application file for complete search history.

(56) References Cited

U.S. PATENT DOCUMENTS

| | | | |
|---|---|---|---|
| 5,415,334 A | 5/1995 | Williamson, IV et al. |
| 5,465,895 A | 11/1995 | Knodel et al. |
| 5,597,107 A | 1/1997 | Knodel et al. |
| 5,632,432 A | 5/1997 | Schulze et al. |
| 5,662,667 A | 9/1997 | Knodel |
| 5,673,840 A | 10/1997 | Schulze et al. |
| 5,673,841 A | 10/1997 | Schulze et al. |
| 5,704,534 A | 1/1998 | Huitema et al. |
| 5,792,135 A | 8/1998 | Madhani et al. |
| 5,814,055 A | 9/1998 | Knodel et al. |
| 5,817,084 A | 10/1998 | Jensen |
| 5,878,193 A | 3/1999 | Wang et al. |
| 6,231,565 B1 | 5/2001 | Tovey et al. |
| 6,364,888 B1 | 4/2002 | Niemeyer et al. |
| 6,783,524 B2 | 8/2004 | Anderson et al. |
| 6,978,921 B2 | 12/2005 | Shelton, IV et al. |
| 7,000,818 B2 | 2/2006 | Shelton, IV et al. |
| 7,044,352 B2 | 5/2006 | Shelton, IV et al. |
| 7,143,923 B2 | 12/2006 | Shelton, IV et al. |
| 7,303,108 B2 | 12/2007 | Shelton, IV |
| 7,367,485 B2 | 5/2008 | Shelton, IV et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,419,080 B2 | 9/2008 | Smith et al. |
| 7,434,715 B2 | 10/2008 | Shelton, IV et al. |
| 7,455,208 B2 | 11/2008 | Wales et al. |
| 7,490,749 B2 | 2/2009 | Schall et al. |
| 7,524,320 B2 | 4/2009 | Tierney et al. |
| 7,549,564 B2 | 6/2009 | Boudreaux |
| 7,644,848 B2 | 1/2010 | Swayze et al. |
| 7,658,311 B2 | 2/2010 | Boudreaux |
| 7,691,098 B2 | 4/2010 | Wallace et al. |
| 7,721,930 B2 | 5/2010 | McKenna et al. |
| 7,753,245 B2 | 7/2010 | Boudreaux et al. |
| 7,798,386 B2 | 9/2010 | Schall et al. |
| 7,806,891 B2 | 10/2010 | Nowlin et al. |
| 7,954,684 B2 | 6/2011 | Boudreaux |
| 8,006,365 B2 * | 8/2011 | Levin ................... A61B 17/064 227/175.1 |
| 8,210,411 B2 | 7/2012 | Yates et al. |
| 8,245,898 B2 | 8/2012 | Smith et al. |
| 8,408,439 B2 | 4/2013 | Huang et al. |
| 8,453,914 B2 | 6/2013 | Laurent et al. |
| 8,479,969 B2 | 7/2013 | Shelton, Iv |
| 8,573,461 B2 | 11/2013 | Shelton, Iv et al. |
| 8,573,465 B2 | 11/2013 | Shelton, Iv |
| 8,579,176 B2 | 11/2013 | Smith et al. |
| 8,602,288 B2 | 12/2013 | Shelton, Iv et al. |
| 8,616,431 B2 | 12/2013 | Timm et al. |
| 8,783,541 B2 * | 7/2014 | Shelton, IV ..... A61B 17/07207 227/175.1 |
| 8,800,838 B2 | 8/2014 | Shelton, Iv |
| 8,820,605 B2 * | 9/2014 | Shelton, IV ......... A61B 17/072 227/175.1 |
| 8,844,789 B2 | 9/2014 | Shelton, Iv et al. |
| 9,186,142 B2 * | 11/2015 | Fanelli ............. A61B 17/07207 |
| 9,301,759 B2 | 4/2016 | Spivey et al. |
| 2007/0073341 A1 | 3/2007 | Smith et al. |
| 2011/0288573 A1 * | 11/2011 | Yates ............... A61B 17/07207 606/170 |
| 2012/0292367 A1 * | 11/2012 | Morgan ............... A61B 17/072 227/175.1 |
| 2014/0171966 A1 | 6/2014 | Giordano et al. |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239041 A1 | 8/2014 | Zerkle et al. |
| 2014/0239042 A1 | 8/2014 | Simms et al. |
| 2014/0239044 A1 | 8/2014 | Hoffman |
| 2014/0305995 A1 * | 10/2014 | Shelton, IV ..... A61B 17/07207 227/180.1 |
| 2016/0220248 A1 * | 8/2016 | Timm ................ A61B 17/0684 227/180.1 |

OTHER PUBLICATIONS

International Search Report and Written Opinion dated May 6, 2014 for Application No. PCT/US2014/016200, 8 pgs.

* cited by examiner

SURGICAL INSTRUMENT END EFFECTOR ARTICULATION DRIVE WITH PINION AND OPPOSING RACKS

This application is a continuation of U.S. application Ser. No. 13/780,067, filed Feb. 28, 2013, issued as U.S. Pat. No. 9,186,142 on Nov. 17, 2015 entitled "Surgical Instrument End Effector Articulation Drive with Pinion and Opposing Racks," issued as U.S. Pat. No. 9,186,142 on Nov. 17, 2015.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010 (now U.S. Pat. No. 8,408,439, issued Apr. 2, 2013); and U.S. Pub. No. 2012/0239012, now U.S. Pat. No. 8,453,914, issued Jun. 4, 2013, entitled "Motor-Driven Surgical Cutting Instrument with Electric Actuator Directional Control Assembly," published Sep. 20, 2012 (now U.S. Pat. No. 8,453,914). The disclosure of each of the above-cited U.S. Patents and U.S. Patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
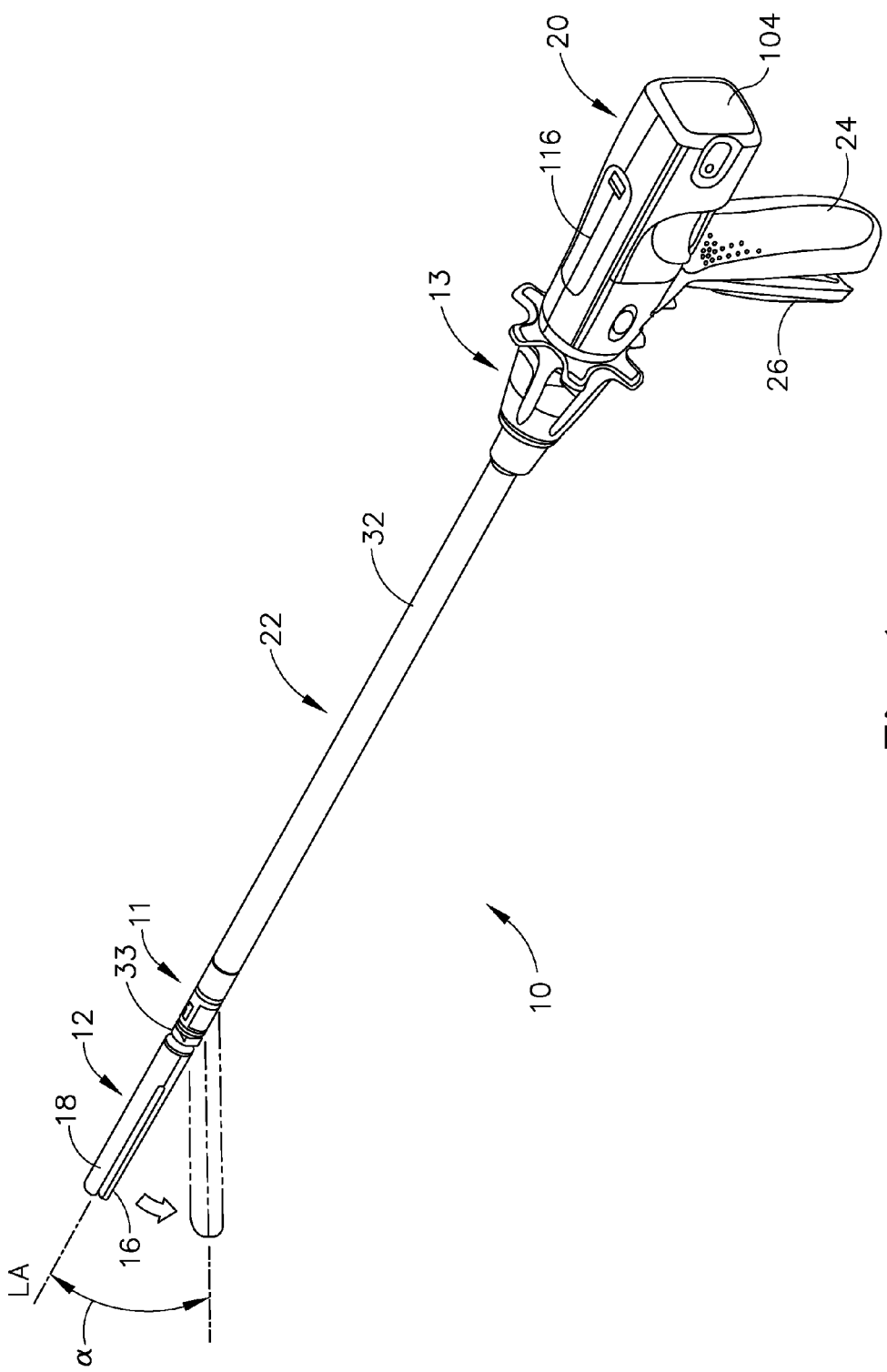
FIG. 1 depicts a perspective view of an exemplary articulating surgical stapling instrument.
Figure 2:
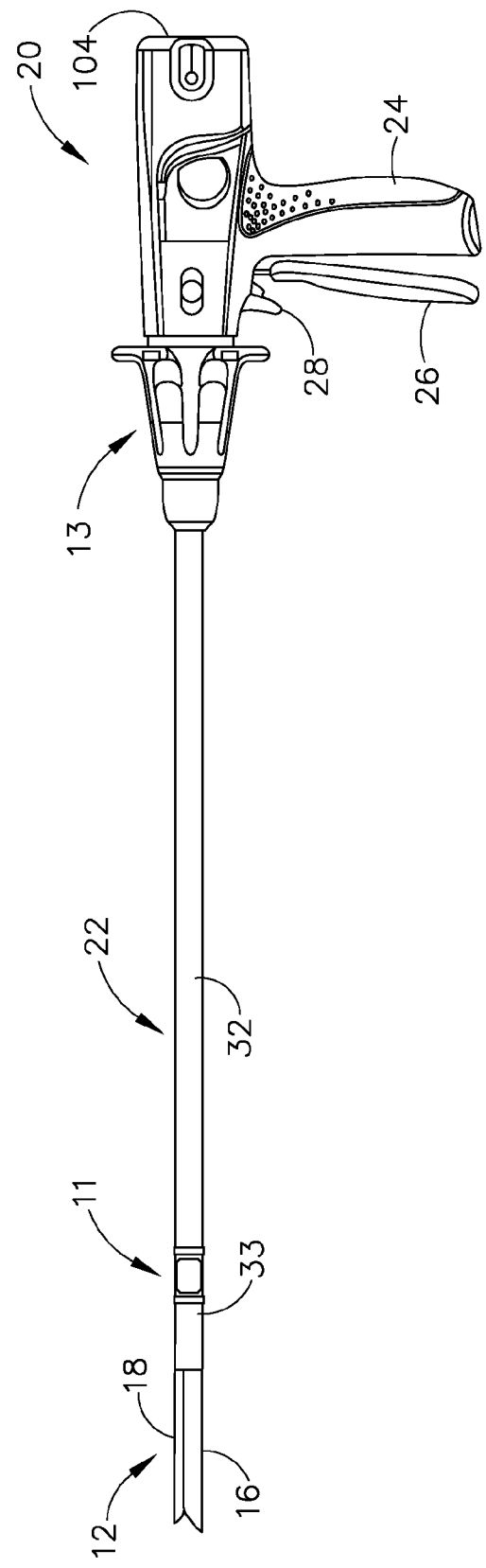
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. patent application Ser. No. 13/780,402 (published as U.S. Pub. No. 2014/0239038 on Aug. 28, 2014), entitled "Surgical Instrument with Multi-Diameter Shaft," filed on Feb. 28, 2013, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

Various exemplary alternative components, configurations, and operabilities of articulation joint (11) and articulation control (13) are described in greater detail below. Articulation joint (11) may also be constructed and operable in accordance with at least some of the teachings of U.S. patent application Ser. No. 13/780,402 (published as U.S. Pub. No. 2014/0239038 on Aug. 28, 2014), the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. patent application Ser. No. 13/780,417 (published as U.S. Pub. No. 2014/0239044), entitled "Installation Features for Surgical Instrument End Effector Cartridge," filed on Feb. 28, 2013 (published Aug. 28, 2014), the disclosure of which is incorporated by reference herein. Anvil (18) may be constructed in accordance with at least some of the teachings of U.S. patent application Ser. No. 13/780,106 (published as U.S. Pub. No. 2014/0239042), entitled "Integrated Tissue Positioning and Jaw Alignment Features for Surgical Stapler," filed on Feb. 28, 2013 (published Aug. 28, 2014), now U.S. Pat. No. 9,517,065, issued Dec. 13, 2016, the disclosure of which is incorporated by reference herein; at least some of the teachings of U.S. Pat. No. 3,780,120 (published as U.S. Pub. No. 2014/0239036), entitled "Jaw Closure Feature for End Effector of Surgical Instrument," filed on Feb. 28, 2013 (published Aug. 28, 2014), the disclosure of which is incorporated by reference herein; and/or at least some of the teachings of U.S. patent application Ser. No. 13/780,379 (published as U.S. Pub. No. 2014/0239037), entitled "Staple Forming Features for Surgical Stapling Instrument," filed on Feb. 28, 2013 (published Aug. 28, 2014), the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44).

Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. patent application Ser. No. 13/780,082 (published as U.S. Pub. No. 2014/0239041), entitled "Lockout Feature for Movable Cutting Member of Surgical Instrument," filed on Feb. 28, 2013 (published Aug. 28, 2014), the disclosure of which is incorporated by reference herein. Other suitable forms that firing beam (14) may take will be apparent to those of ordinary skill in the art in view of the teachings herein.

Figure 3:
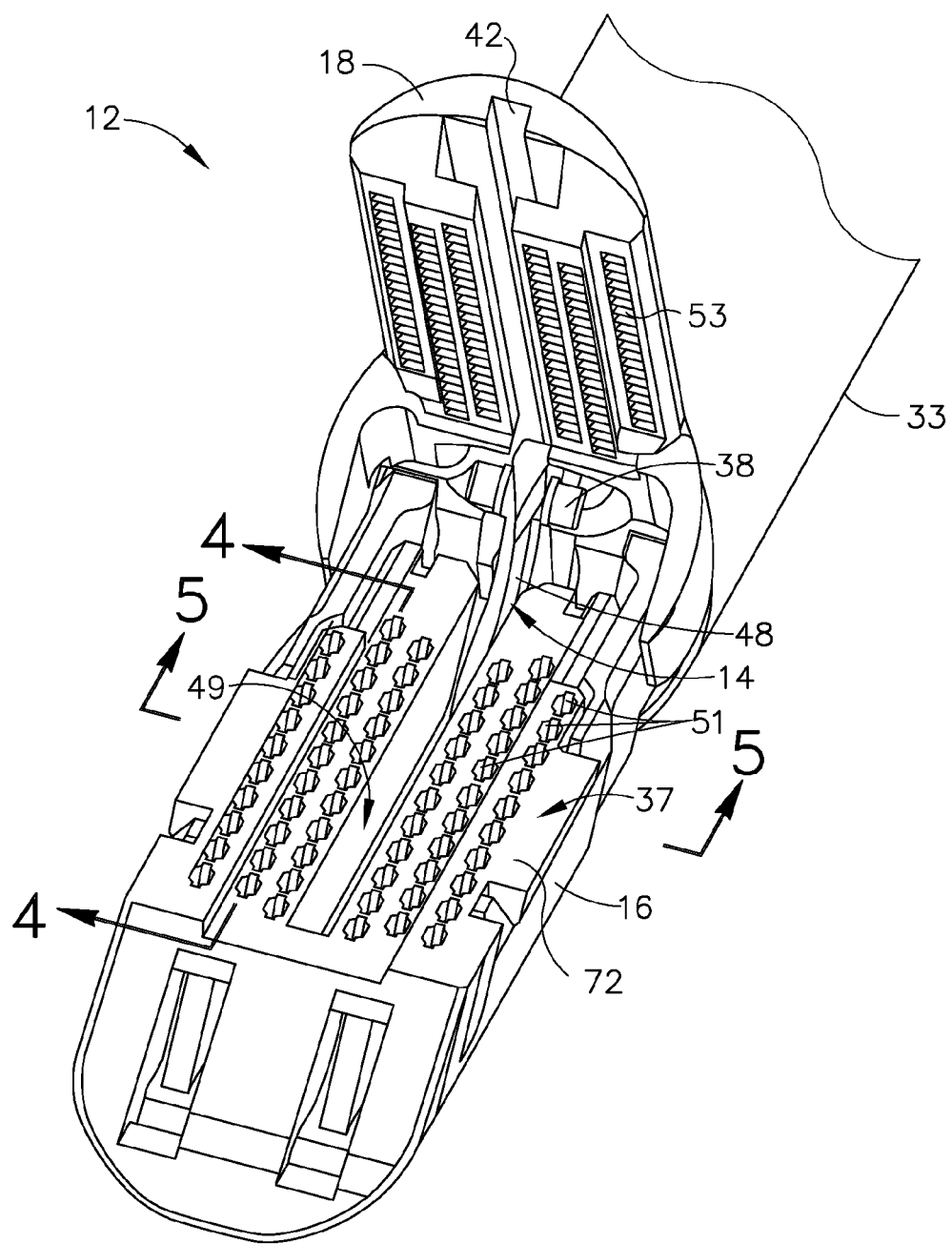
FIG. 3 depicts a perspective view of an opened end effector of the instrument of FIG. 1.
Figure 4A:
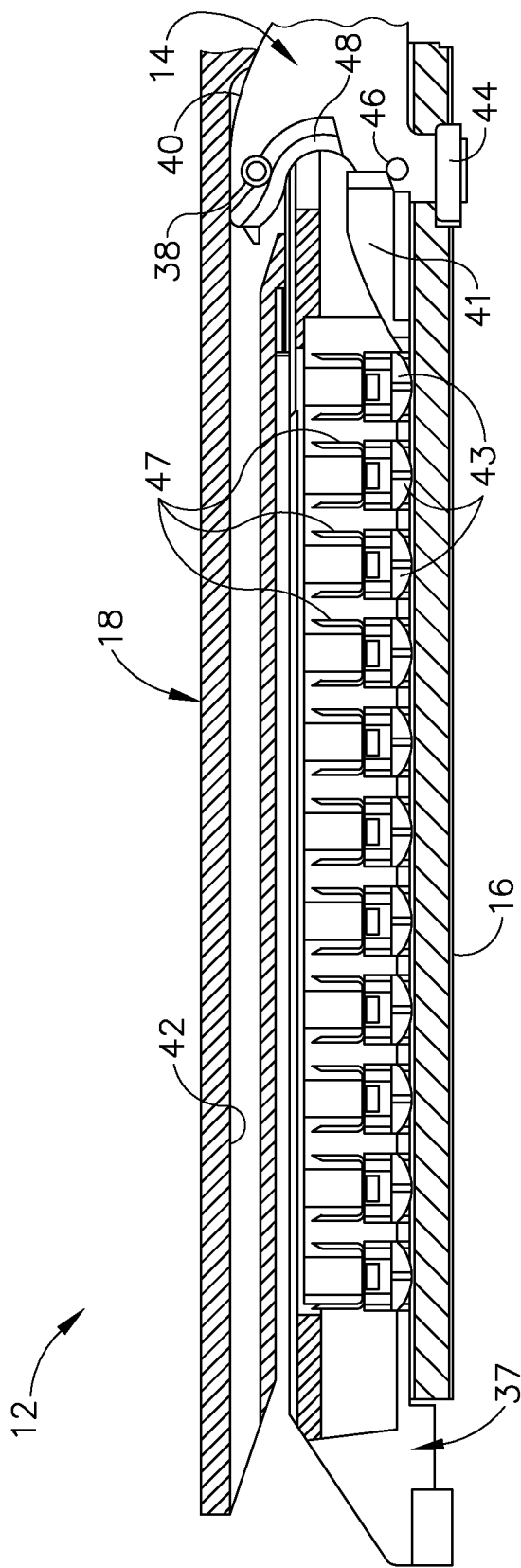
FIG. 4A depicts a side cross-sectional view of the end effector of FIG. 3, taken along line 4-4 of FIG. 3, with the firing beam in a proximal position.
Figure 4B:
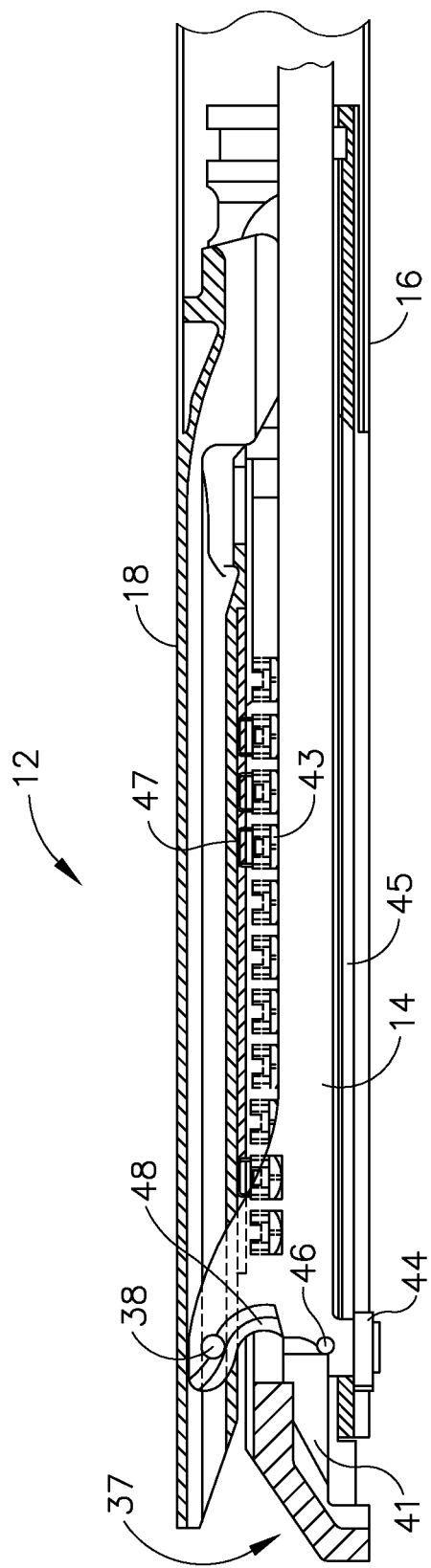
FIG. 4B depicts a side cross-sectional view of the end effector of FIG. 3, taken along line 4-4 of FIG. 3, with the firing beam in a distal position.
Figure 5:
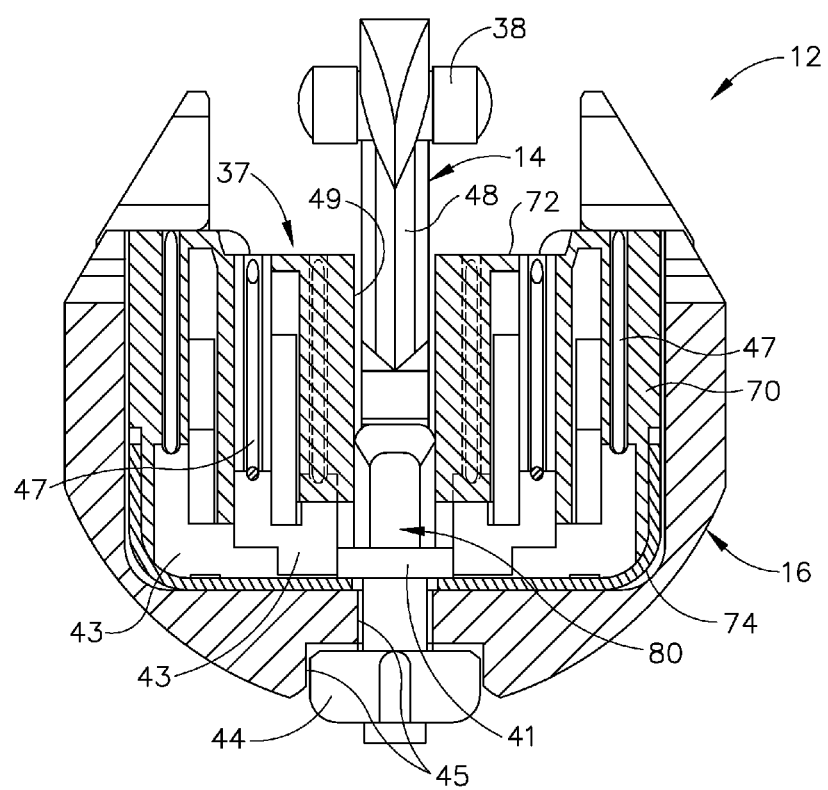
FIG. 5 depicts an end cross-sectional view of the end effector of FIG. 3, taken along line 5-5 of FIG. 3.
Figure 6:
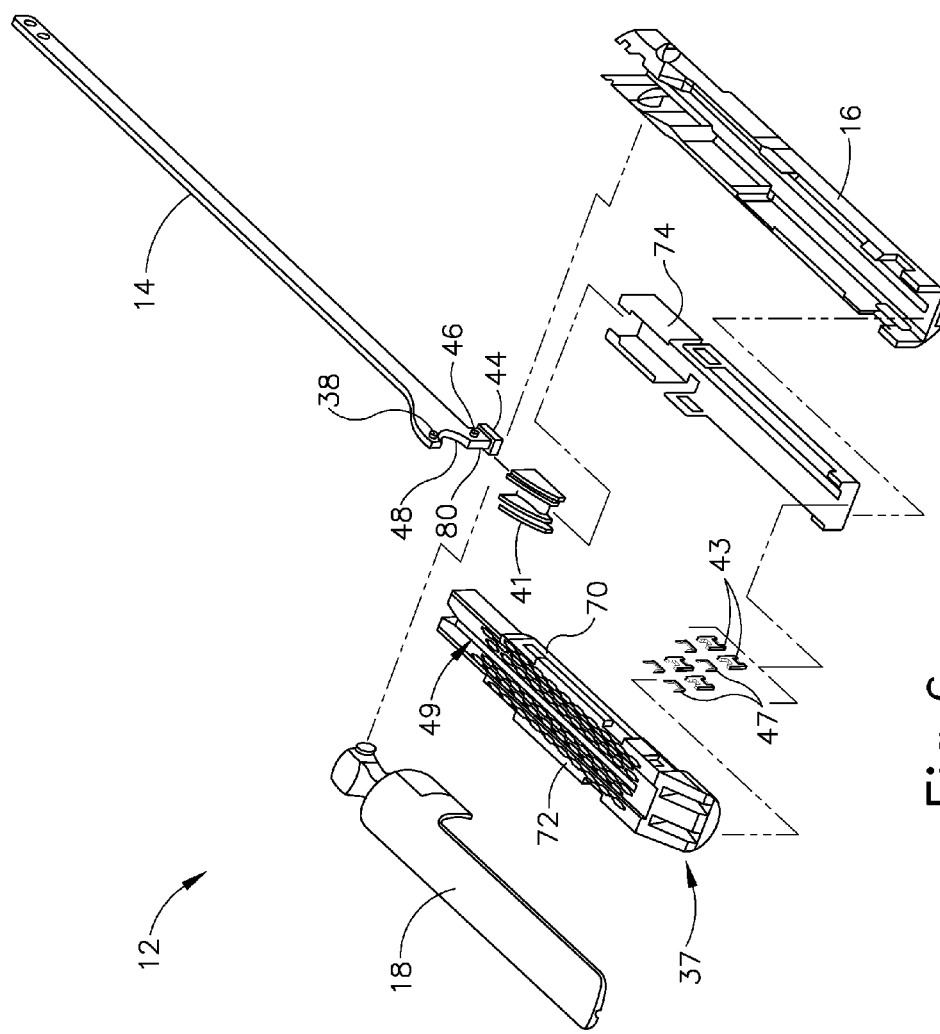
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. patent application Ser. No. 13/780,106 (published as U.S. Pub. No. 2014/0239042), now U.S. Pat. No. 9,517,065, issued Dec. 13, 2016 the disclosure of which is incorporated by reference herein. In addition or in the alternative, staple cartridge (37) may be constructed and operable in accordance with at least some of the teachings of U.S. patent application Ser. No. 13/780,417 (published as U.S. Pub. No. 2014/0239044 on Aug. 28, 2014), the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
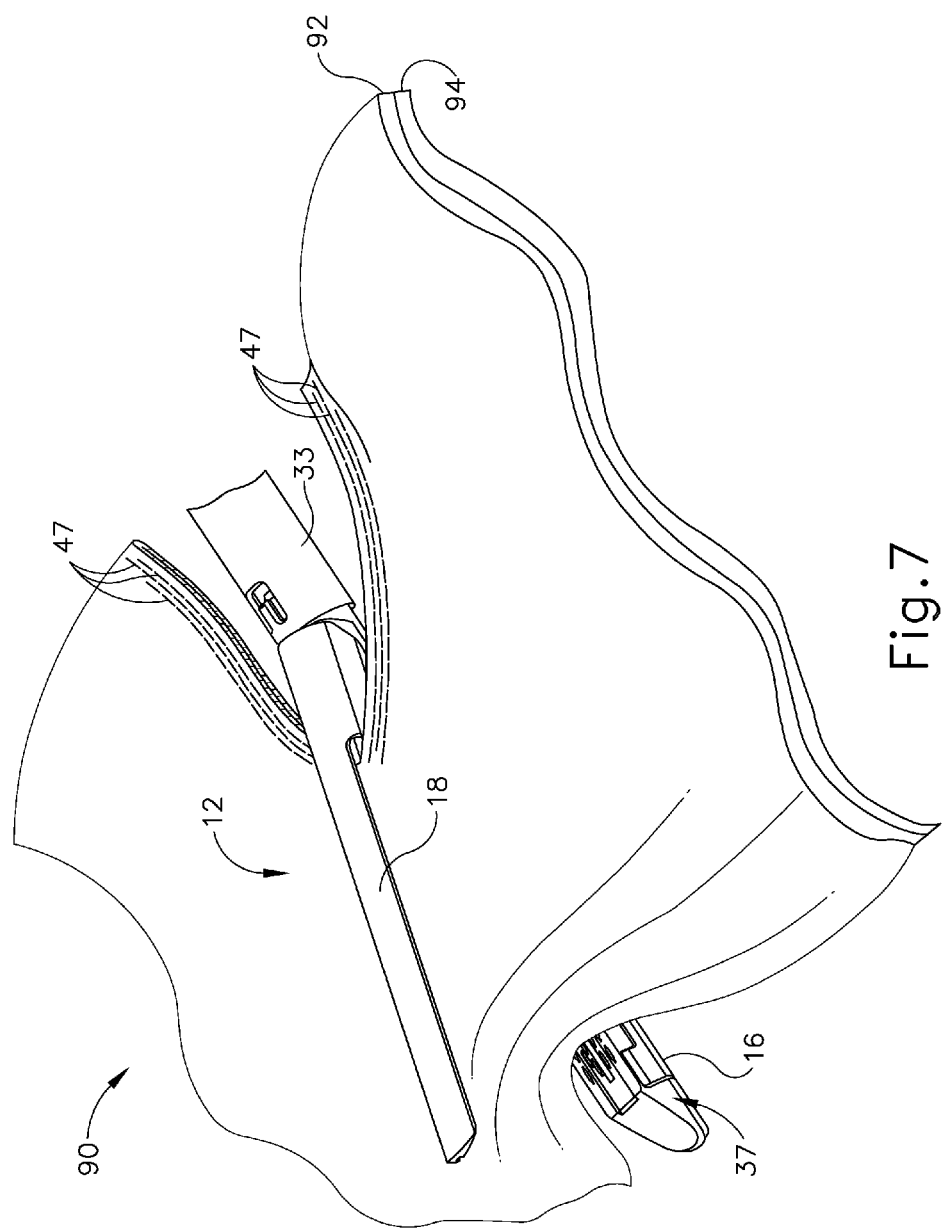
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; U.S. Pub. No. 2010/0264193 (now U.S. Pat. No. 8,408,439, issued Apr. 2, 2013); and/or 2012/0239012 (now U.S. Pat. No. 8,453,914, issued Jun. 4, 2013). As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
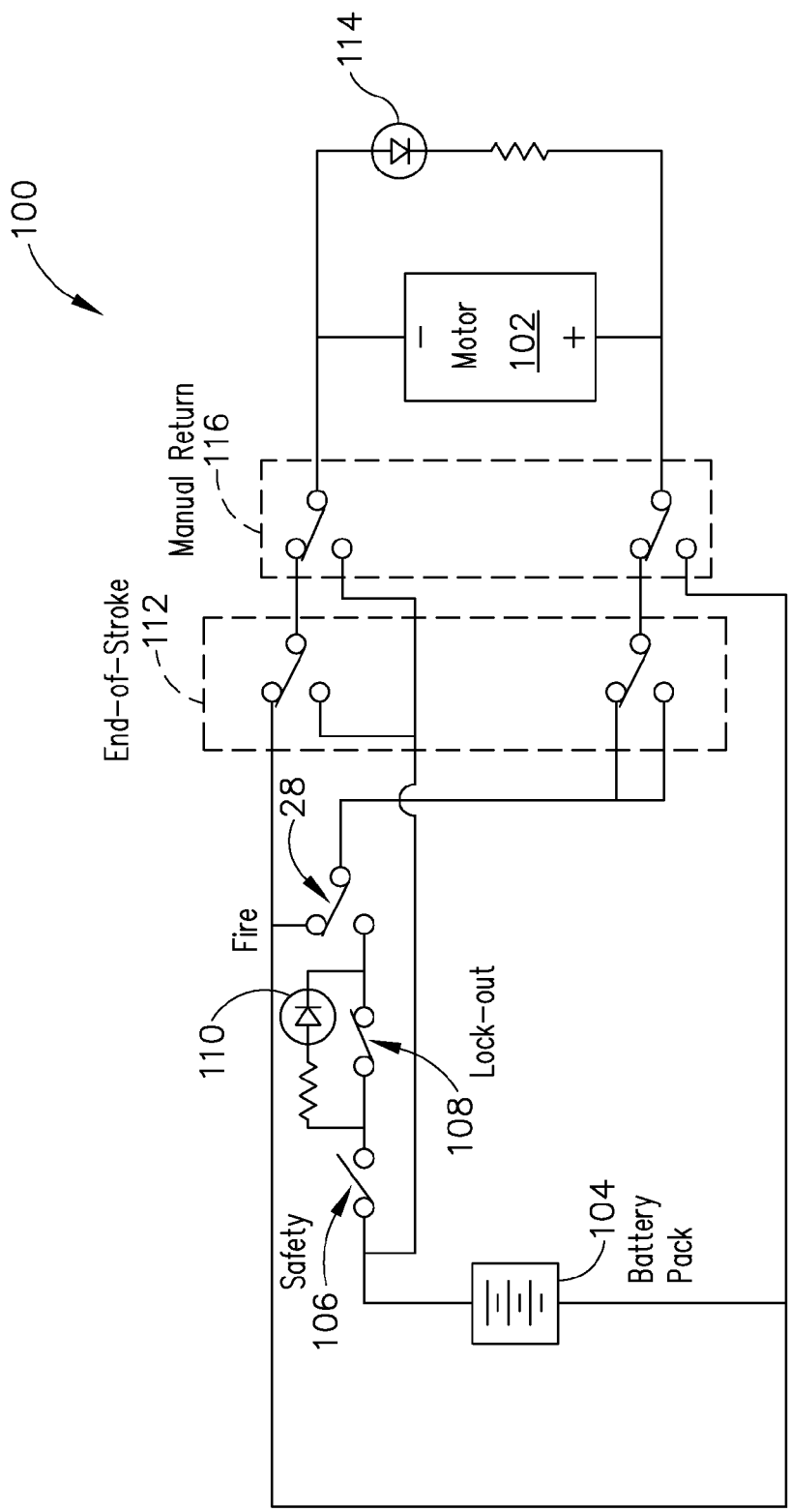
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat.

No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
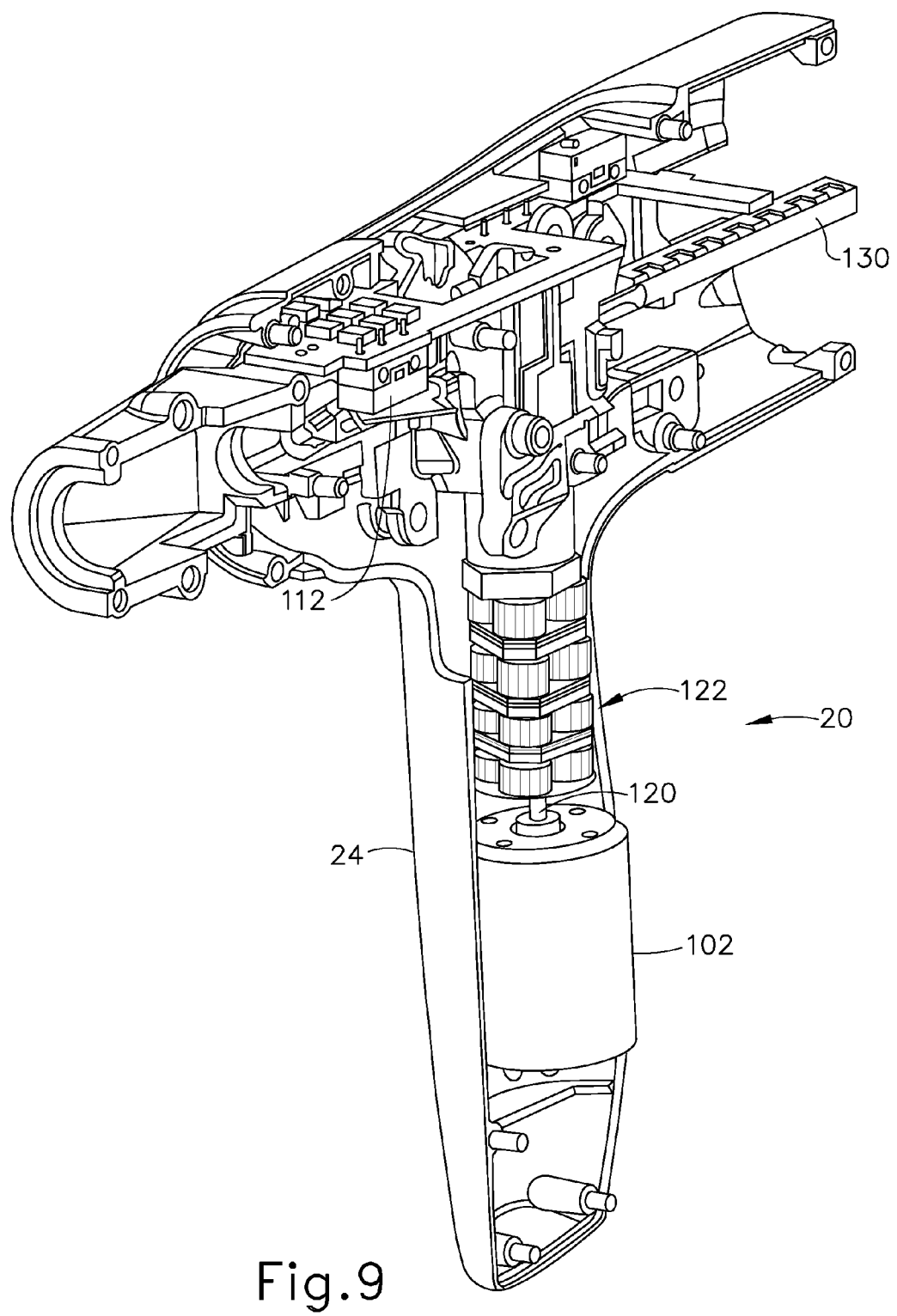
FIG. 9 depicts a perspective view of the handle assembly of the instrument of FIG. 1, with a housing half removed.
Figure 10:
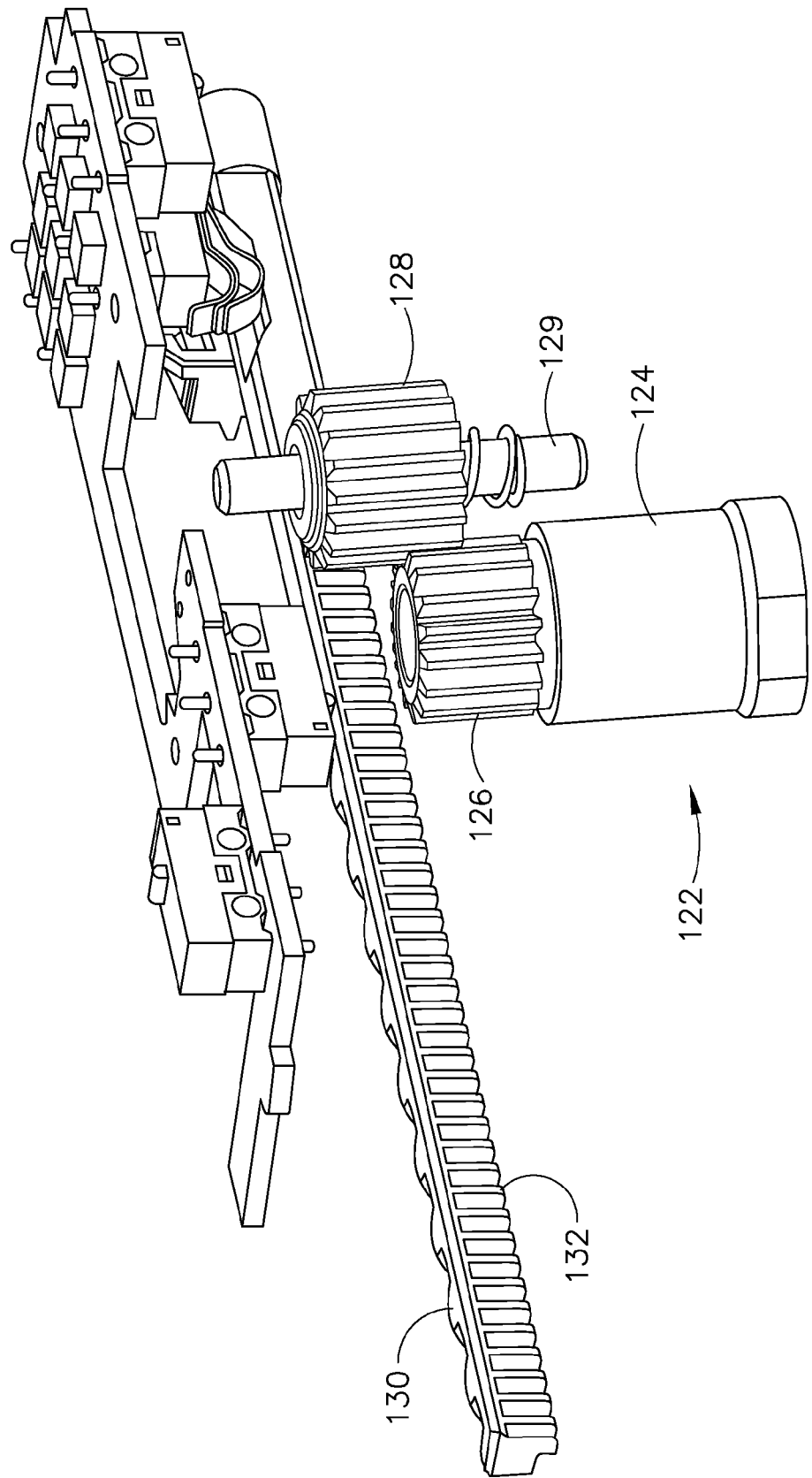
FIG. 10 depicts a perspective view of drive assembly components from the handle assembly of FIG. 9.
Figure 11:
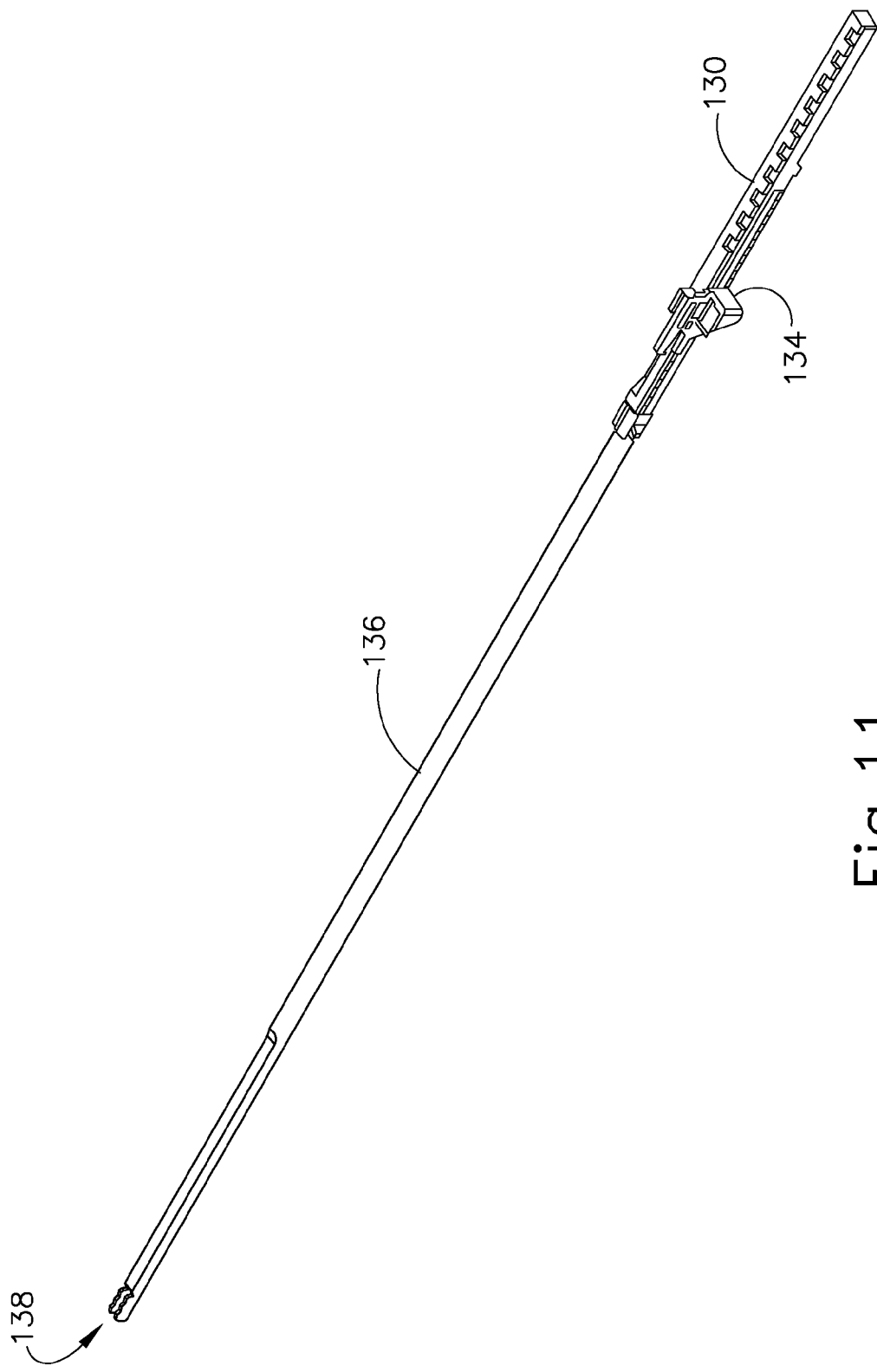
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14) within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012 (now U.S. Pat. No. 8,453,914, issued Jun. 4, 2013), the disclosure of which is incorporated by reference herein; and/or in accordance with at least some of the teachings of U.S. Pub. No. 2012/0239012 (now U.S. Pat. No. 8,453,914, issued Jun. 4, 2013), the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary Shaft Assembly

It will be appreciated that as a user urges instrument (10) into a surgical region, it may be desirable to approach the tissue to be clamped, stapled, or cut, from a particular angle. For instance, once end effector (12) of instrument (10) is inserted through a trocar, thoracotomy, or other passageway for entering a surgical area, the tissue that the user wishes to target may be positioned out of reach or at an askew angle in relation to end effector (12) that is aligned with shaft (22). Thus, it may be desirable for portions of instrument (10), such as end effector (12), to articulate such that the user can position anvil (18) and lower jaw (16) of end effector (12) to squarely or perpendicularly clamp against a vessel or other tissue. It will further be understood that articulating end effector (12) to squarely position end effector (12) against tissue may promote full seating and clamping of the tissue prior to cutting and stapling tissue. In addition to articulating, it may be desirable for end effector (12) to be selectively locked in a straight or articulated position such that a constant manual bias by the user is not necessary to prevent end effector (12) from pivoting or bending at articulation joint (11). It may also be desirable to automatically lock upon articulation, without requiring actuations of a separate articulation locking feature.

Figure 12:
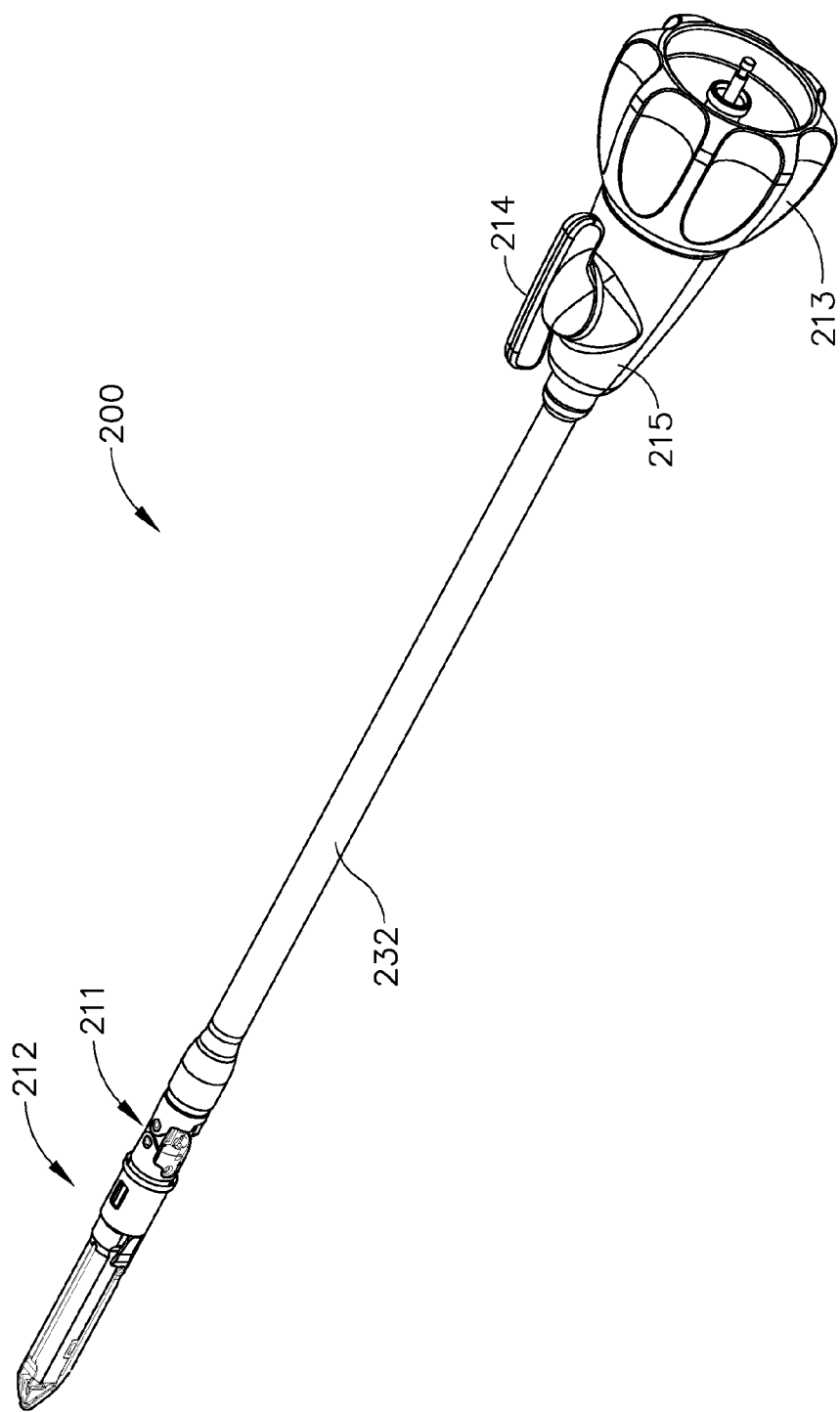
FIG. 12 depicts a top, perspective view of an exemplary alternative shaft assembly that may be incorporated into the instrument of FIG. 1.

FIG. 12 depicts an exemplary alternative shaft assembly (200) that may be readily incorporated with instrument (10) of FIG. 1. Shaft assembly (200) provides articulation and selective locking of articulation angles, as will be described in greater detail below. Shaft assembly (200) of the present example comprises a rotation control (213), and articulation knob (214), and an end effector (212). Rotation control (213) may be rotatably coupled with handle portion (20) of FIG. 1 or any other suitable component (e.g., robotic control interface, etc.). Rotation control (213) is operable to rotate shaft assembly (200) (including articulation knob (214) and end effector (212)) about the longitudinal axis (LA) defined by shaft assembly (200), relative to handle portion (20) (or relative whatever else rotation control (213) is rotatably coupled with). This may be useful in positioning end effector (212) at a desired angular orientation about the longitudinal axis (LA).

Articulation knob (214) is partially contained within an articulation knob casing (215). Casing (215) leads to an elongate shaft (232). Shaft assembly (200) also comprises an end effector (212) positioned distally in relation to shaft (232). End effector (212) includes an articulation joint (211) which allows end effector (212) to articulate laterally as will be described in further detail below. End effector (212) is substantially identical to end effector (12) of FIG. 1 except as otherwise described below.

Figure 13A:
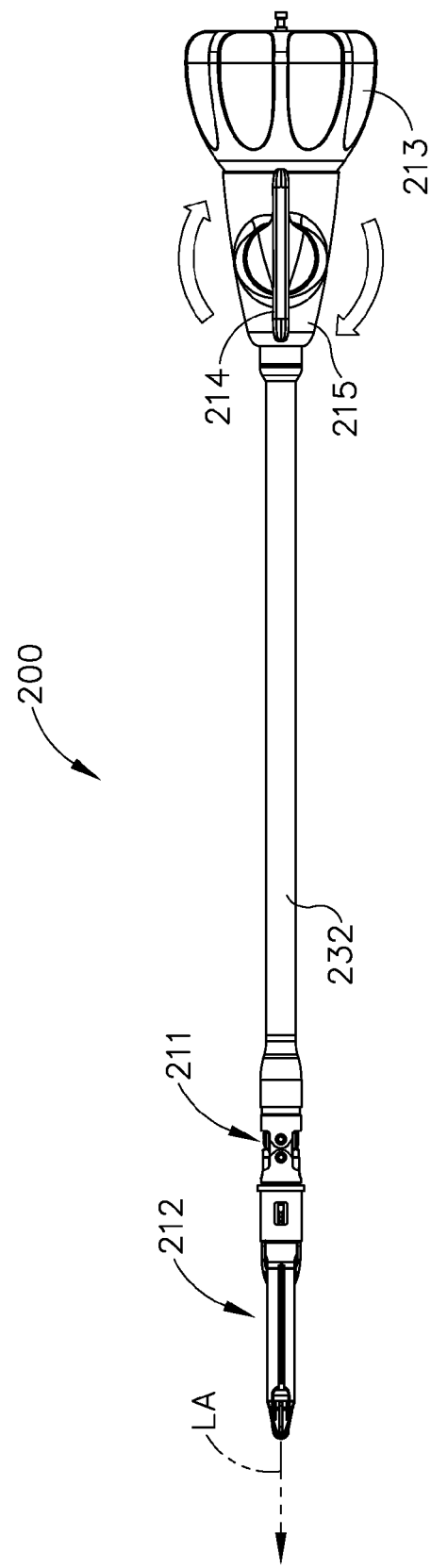
FIG. 13A depicts a top, plan view of the shaft assembly of FIG. 12 with the end effector in a first position.
Figure 13B:
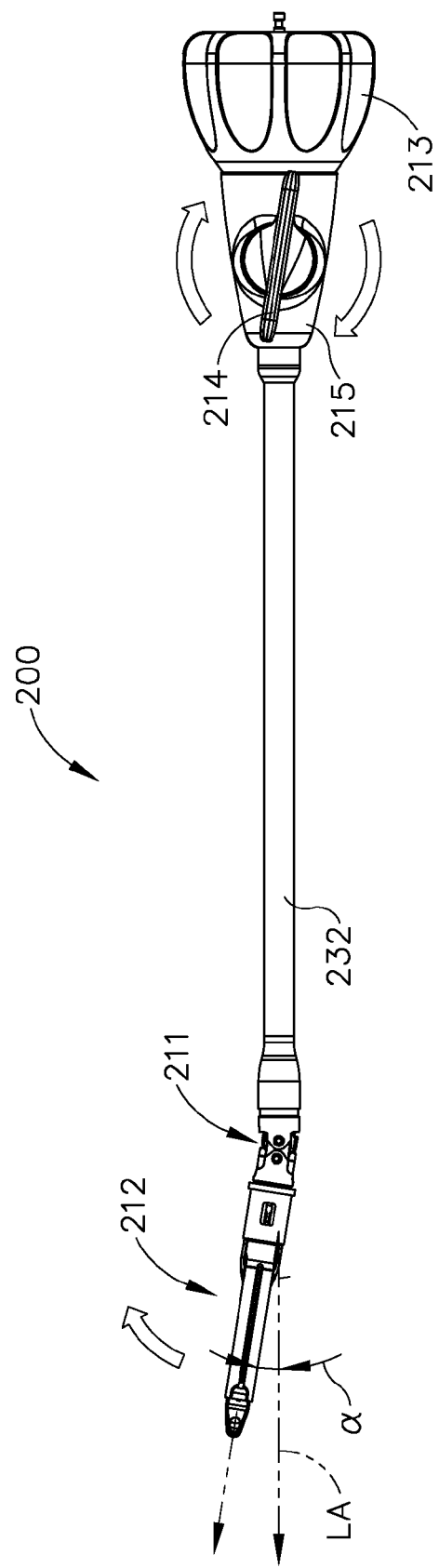
FIG. 13B depicts a top, plan view of the shaft assembly of FIG. 12 with the end effector in a second articulated position.

FIGS. 13A-B show shaft assembly (200) and an exemplary movement of end effector (212) in response to turning of articulation knob (214). FIG. 13A shows articulation knob (214) in a first position where articulation knob (214) and end effector (212) are both generally aligned along the longitudinal axis (LA) of shaft assembly (200). The user may then manually rotate articulation knob (214) clockwise as seen in FIG. 13B to a second position. In response to the rotation of articulation knob (214), end effector (212) pivots or bends at articulation joint (211) as seen in FIG. 13B to an articulation angle (a). In the illustrated version, end effector (212) articulates generally in the direction of the rotation of articulation knob (214), though it will be understood that end effector (212) may be configured to bend in the opposite direction of the rotation of articulation knob (214). In other words, when articulation knob (214) is rotated clockwise, end effector (212) laterally pivots clockwise as shown in FIG. 13B but could be configured in some versions to pivot counter clockwise. FIG. 13B shows end effector (212) laterally pivoting clockwise slightly. It will be understood that articulation knob (214) may be rotated further to cause end effector (212) to laterally articulate further at articulation joint (211) to any suitable angle (a). For instance, end effector (212) may pivot until an approximately 90° angle is formed across articulation joint (211). In some versions, end effector (212) may be operable to pivot even further such that end effector (212) forms an acute angle in relation to shaft (232). Other suitable variations of end effector (212) pivoting will be apparent to one of ordinary skill in the art in view of the teachings herein. It should also be understood that articulation knob (214) may define the same angle with the longitudinal axis (LA) as the articulation angle (a) defined between end effector (212) and the longitudinal axis (LA). Such complementary angling may provide the operator with visual feedback exterior to the patient, indicating the articulation angle (a) of end effector (212).

The mechanics of the articulation of end effector (212) will be discussed in further detail below. It will be appreciated that articulation knob (214) may be rotated in the counter clockwise direction to cause end effector (212) to articulate in a counter clockwise manner. Thus, depending on the desired direction and/or amount of articulation of end effector (212), the user can simply rotate articulation knob (214) of varying degrees in the direction that the user wishes end effector (212) to articulate to cause varying degrees of articulation of end effector (212).

Figure 14:
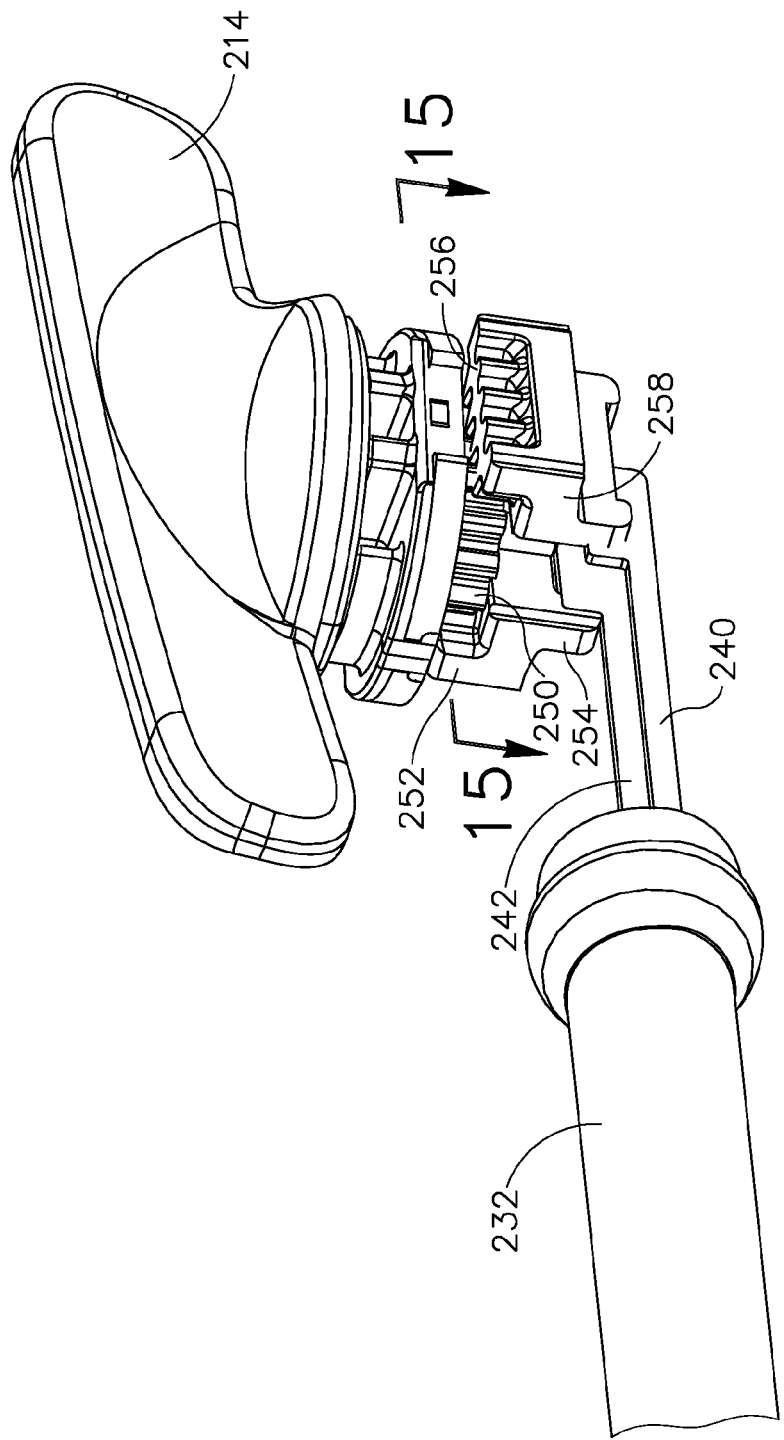
FIG. 14 depicts a perspective view of the proximal end of the shaft assembly of FIG. 12 showing the articulation knob and internal kinematic components.

FIG. 14 shows articulation knob (214) with casing (215) removed to better show the inner workings of articulation knob (214). Articulation knob (214) is in communication with an articulation pinion (250). Articulation pinion (250) is in communication with a first rack (252) and a second rack (256). First rack (252) is in communication with a first arm (242) through a first intermediate block (254), whereas second rack (256) is in communication with a second arm (240) through a second intermediate block (256).

Figure 15:
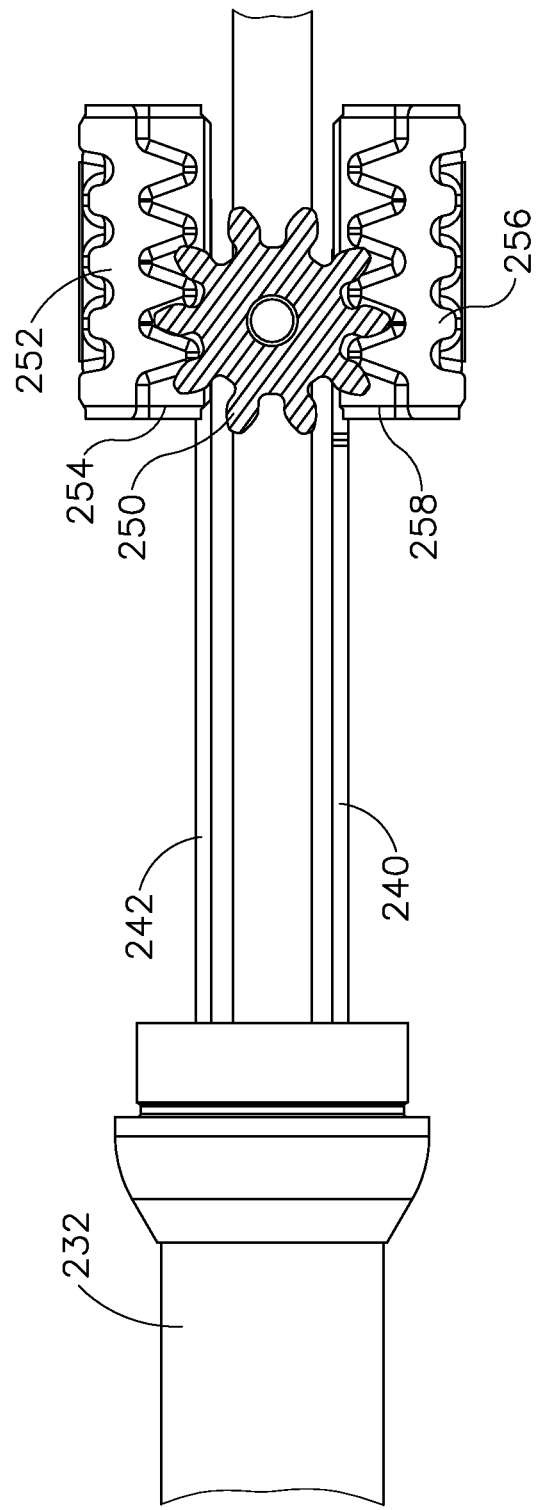
FIG. 15 depicts a top cross sectional view of the proximal end of the shaft assembly of FIG. 12 taken along the line 15-15 of FIG. 14.

Articulation knob (214) is unitarily coupled to articulation pinion (250). As a result, when the user turns articulation knob (214), articulation pinion (250) rotates together with articulation knob (214). As articulation pinion (250) rotates, articulation pinion (250) translates first rack (252) and second rack (256) accordingly in opposing directions. For instance, as seen in FIG. 15, articulation pinion (250) is in communication with first rack (252) and second rack (256) such that if articulation pinion (250) rotates clockwise, first rack (252) retracts proximally away from end effector (212) whereas second rack (256) advances distally toward end effector. Furthermore, when articulation pinion (250) rotates counter-clockwise, first rack (252) advances distally toward end effector (212) and second rack (256) retracts proximally away from end effector (212). As first rack (252) advances and retracts, first arm (242) advances and retracts in a similar fashion. Similarly, as second rack (256) advances and retracts, second arm (240) also advances and retracts with second rack (256). Thus, rotating articulation knob (214), which is connected to articulation pinion (250), causes first arm (242) and second arm (240) to move back and forth with first rack (252) and second rack (256). Movement of first arm (242) and second arm (240) is operable to cause movement of other components in end effector (212), which will be discussed in further detail below.

Figure 16:
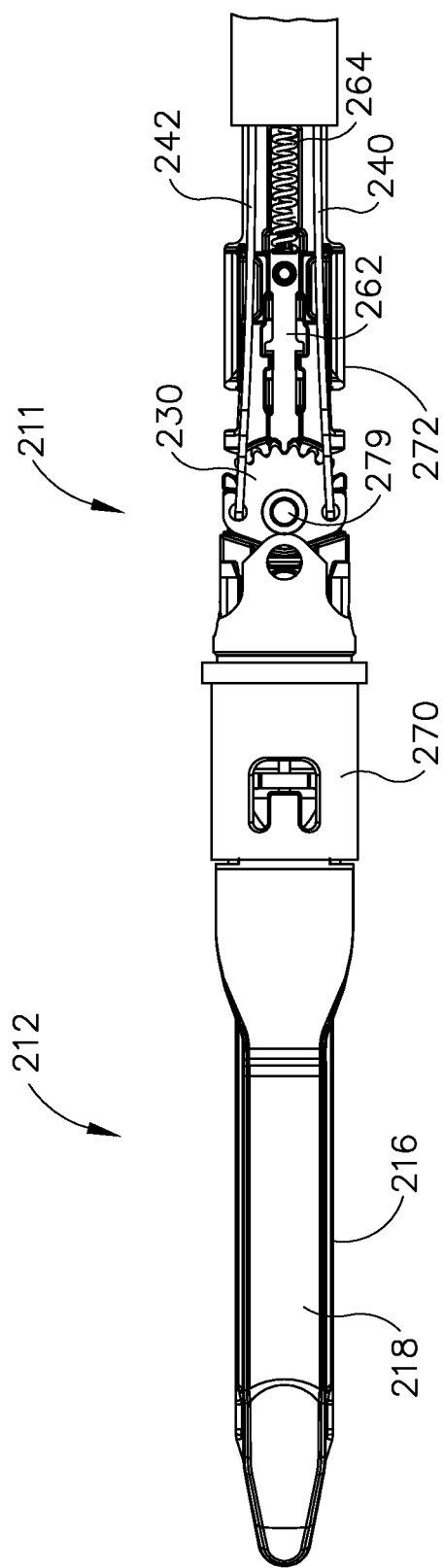
FIG. 16 depicts a top, plan view of the shaft assembly of FIG. 12 in a neutral position.

FIG. 16 shows a larger view of end effector (212), including anvil (218). First arm (242) and second arm (240) are in communication with a first cam gear (230). As a result, advancing and retracting first arm (242) and second arm (240) causes first cam gear (230) to rotate, which will be described in further detail below.

Figure 17:
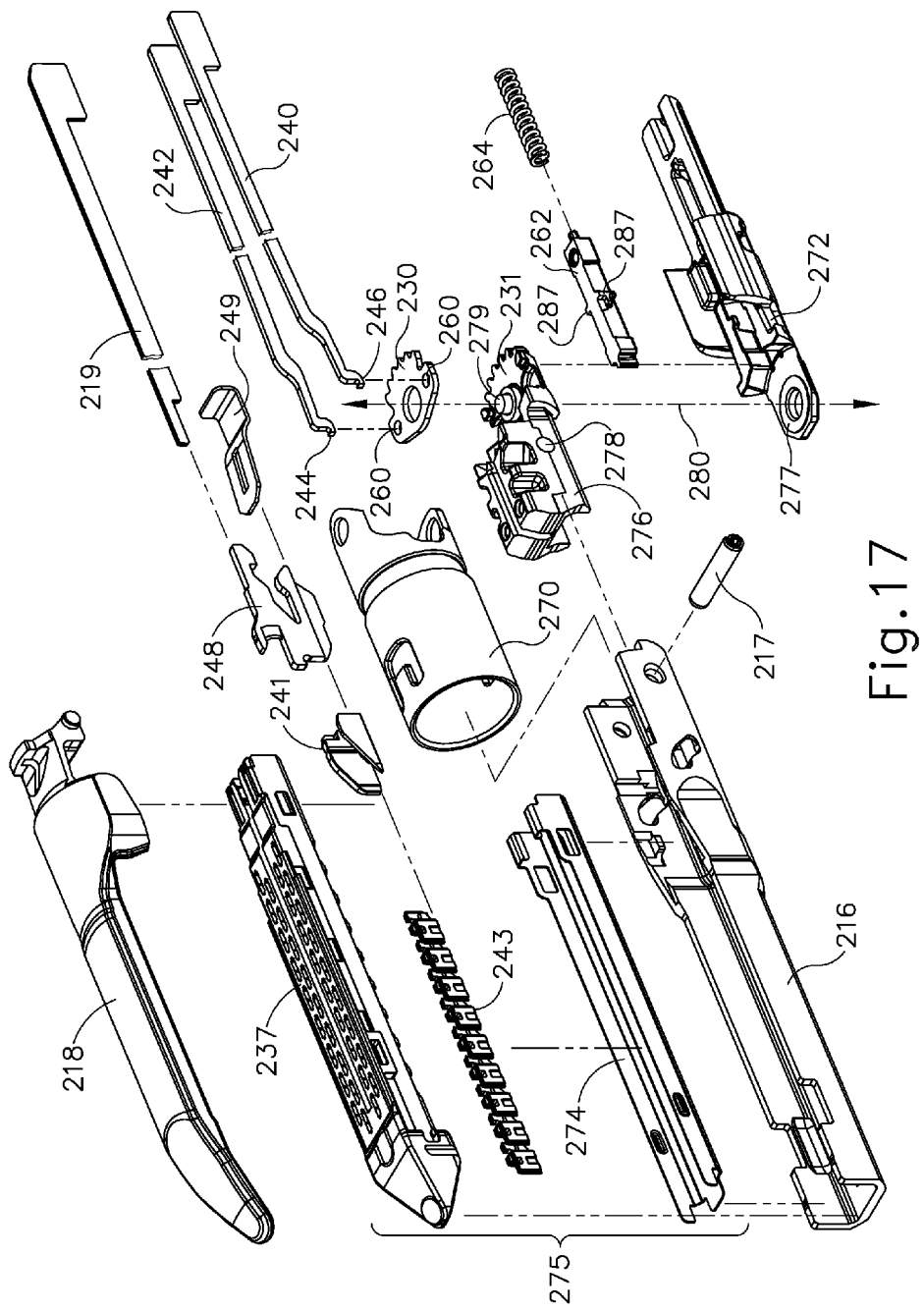
FIG. 17 depicts a perspective, exploded view of the end effector and the articulation joint of the shaft assembly of FIG. 12.

FIG. 17 shows an exploded view of end effector (212) and articulation joint (211). End effector (212) comprises an anvil (218), a lower jaw (216), and a staple cartridge (275). Cartridge (275) comprises staple drivers (243), a cartridge body (237), a tray (274), and wedge sled (241). It will be appreciated that anvil (218), lower jaw (216), tray (274), cartridge body (237), and wedge sled (241) are substantially similar to anvil (18) lower jaw (16), tray (74), cartridge (37), and wedge sled (41) shown in FIG. 6. Generally, tray (274) is removably received in lower jaw (216); and tray (274), cartridge body (237), and staple drivers (243) snap together to form staple cartridge (275). The proximal portions of anvil (218) and lower jaw (216) fit within jaw sleeve (270), which is in communication with articulation joint (211). Anvil (218) is operable to close against cartridge body (237)

in response to distal advancement of jaw sleeve (270), such that anvil (218) and cartridge body (237) can clamp tissue, which may then be stapled and cut. In particular, after clamping tissue, wedge sled (241) is driven distally, which urges staple drivers (243) upwardly, which drives staples (not shown, but would otherwise be positioned above staple drivers (243)) through tissue and against anvil (218), anchoring the staples in tissue. Sled (241) in the illustrated version is driven by a knife (248), which is secured to and driven by a firing beam (219). As firing beam (219) advances, knife (248) cuts tissue while driving sled (241).

End effector (212) of the present example further comprises resilient a lockout feature (249) that is operable to cooperate with cam holding body (276) to selectively restrict advancement of knife (248) in the absence of an unfired cartridge (275) being loaded in lower jaw (216). By way of example only, lockout feature (249) and associated components may be configured and operable in accordance with at least some of the teachings of U.S. patent application Ser. No. 13/780,082 (published as U.S. Pub. No. 2014/0239041), entitled "Lockout Feature for Movable Cutting Member of Surgical Instrument," filed on Feb. 28, 2013 (published Aug. 28, 2014), the disclosure of which is incorporated by reference herein.

Articulation joint (211) comprises several components that will be discussed in further detail below. Generally speaking, articulation joint (211) comprises first cam gear (230), second cam gear (231), cam holding body (276), a channel pin (217), joint base (272), a lock bar (262), and a spring (264).

First arm (242) distally terminates in to a first hook (244), while second arm (240) distally terminates in a second hook (246). Hooks (244, 246) are in communication with cam openings (260) of first cam gear (230). As a result, when first arm (242) advances toward end effector (212) and second arm (240) retracts, first cam gear (230) rotates counter clockwise. When first arm (242) instead retracts and second arm (240) advances toward end effector (212), first cam gear (230) rotates clockwise. Thus, as arms (242, 240) push and pull on cam openings (260) via hooks (244, 246), first cam gear (230) rotates accordingly as just described.

First cam gear (230) is stacked on a second cam gear (231). Second cam gear (231) and cam holding pin (279) are unitary features of cam holding body (276). In some versions, second cam gear (231) may be separately constructed and fixedly coupled with cam holding body (276), such that as second cam gear (231) rotates, cam holding body (276) rotates. First cam gear (230) is rotationally coupled with cam holding pin (279), which is coaxially aligned with base opening (277) of joint base (272) along a pivot axis (280). Thus, first cam gear (230) is rotatable about pivot axis (280), relative to second cam gear (231) and cam holding body (276). Lock bar (262) is in selective communication with first cam gear (230) and second cam gear (231), which will be described further below. Lock bar (262) is further in communication with spring (264), which distally biases lock bar (262). Joint base (272) is shaped to provide a seat and/or channel for lock bar (262) to advance. Lock bar (262) further includes a pair of bosses (287) operable to engage joint base (272) to restrict distal motion of lock bar (262).

IV. Exemplary Movement of the Shaft Assembly

As discussed above, actuating articulation knob (214) is operable to cause opposing advancement and retraction of arms (242, 240). It will be understood that this motion of arms (242, 240) is operable to rotate first cam gear (230) about cam holding pin (279). As a result of rotating first cam gear (230), second cam gear (231) rotates with cam holding body (276). Thus, articulation joint (211) articulates, thereby pivoting end effector (212) at articulation joint (211). In particular, cam holding pin (279) and base opening (274) define a pivot axis (280), which is generally perpendicular to the longitudinal axis (LA). End effector (212) pivots about pivot axis (280) in response to the rotation of first cam gear (230), which drives second cam gear (231) as will be discussed below. FIGS. 18A-E illustrate the details of rotating first cam gear (230) to drive the articulation of end effector (212).

Figure 18A:
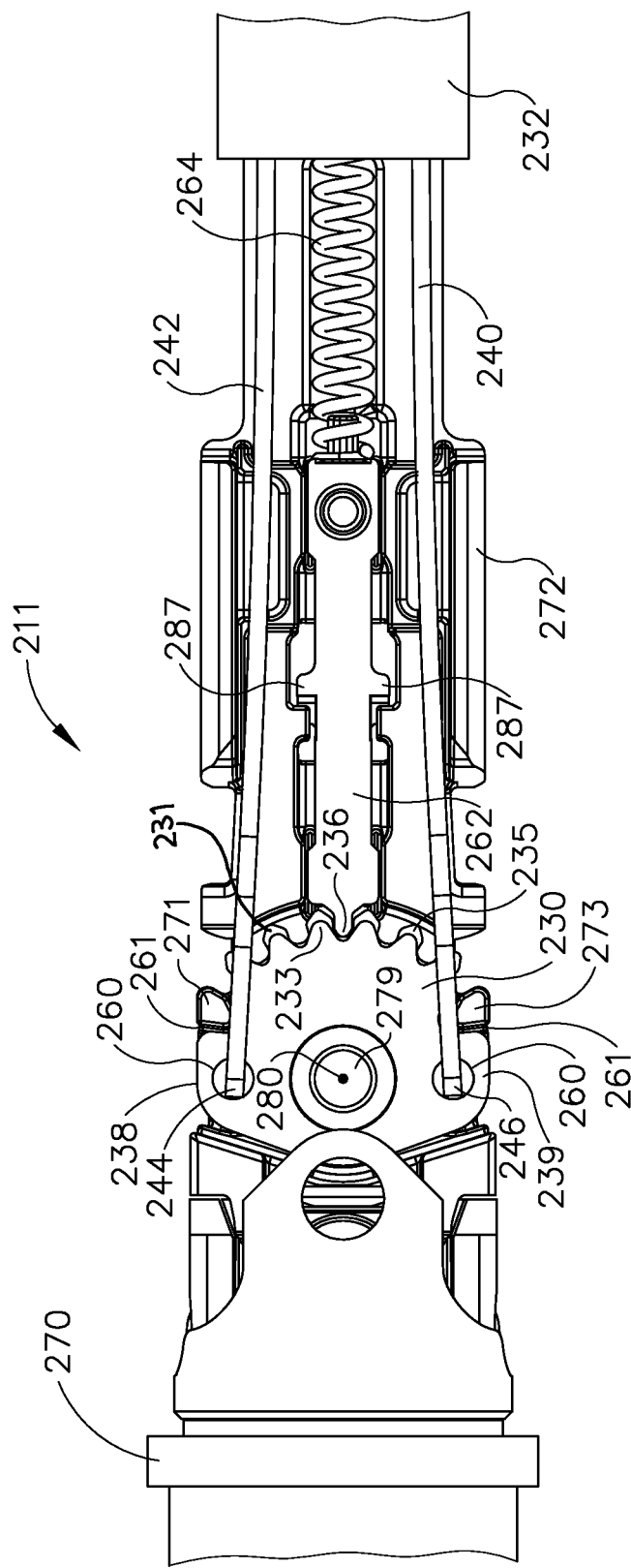
FIG. 18A depicts a top, partially internal view of the articulation joint of the shaft assembly of FIG. 12 in a first position.

FIG. 18A shows articulation joint (211) in a first position. Lock bar (262) is distally biased to engage second cam gear (231). In particular, the distal end of lock bar (262) comprises a lock tooth (236) that fits between first cam teeth (233) and second cam teeth (235) and abuts second cam gear (231), which can be seen in further detail in FIG. 19. As a result of the distal bias provided by spring (264), lock tooth (236) acts as a positive lock and thus maintains the rotational position of second cam gear (231). By maintaining the rotational position of second cam gear (231), lock bar (262) maintains the angular position of end effector (212) about pivot axis (280), thereby maintaining any articulation angle (a). First cam gear (230) comprises a pair of cam wings (238, 239), and cam holding body (276) comprises a pair of bosses (271, 273). Bosses (271, 273) are unitary features of second cam gear (231) such that as bosses (271, 273) rotate, second cam gear (231) also rotates. It will be appreciated that in the first position of FIG. 18A, cam wings (238, 239) and bosses (271, 273) define a small gap (261) therebetween. As a result, cam wings (238, 239) and bosses (271, 273) are not in contact. The interaction involving contact between cam wings (238, 239) and bosses (271, 273) will be described in further detail below with reference to FIGS. 18B-E. During a surgical operation, the user may guide shaft assembly (200) through a passageway (e.g. trocar, thoracotomy, etc.) to reach the surgical area with end effector (212) in a straightened position as shown in FIG. 18A.

Figure 19:
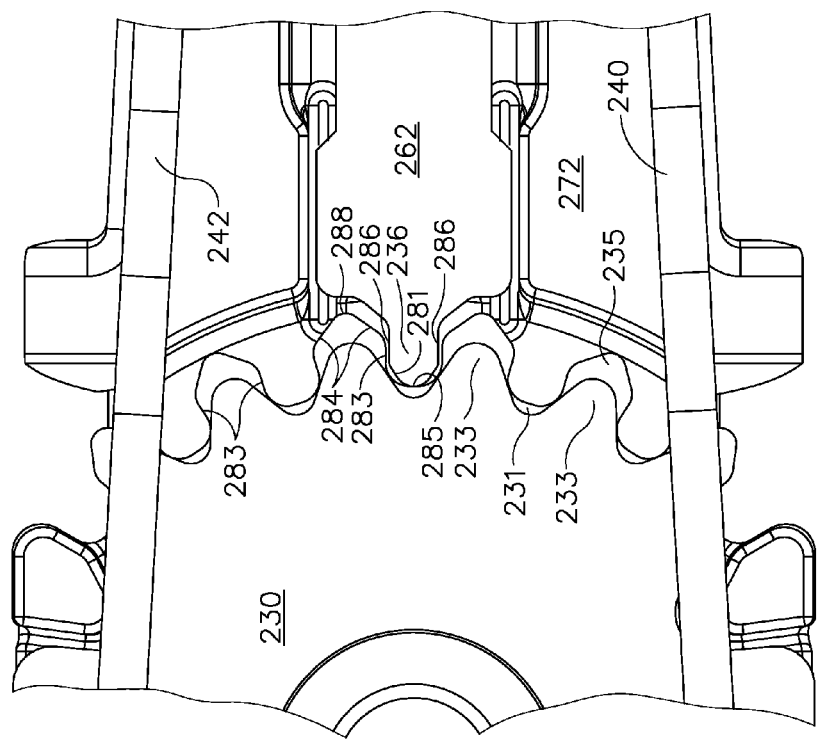
FIG. 19 depicts a plan, enlarged view of the interface of the cam gears and the lock bar of the shaft assembly of FIG. 12.

FIG. 19 shows an enlarged view of lock tooth (236) in the position shown in FIG. 18A. As can be seen in the illustrated version, lock tooth (236) has generally straight parallel sides (286) that are operable to fit between first cam teeth (233) and second cam teeth (235). The distal end of lock tooth (236) has a rounded tip (285) with angled sides (281) leading to parallel sides (286). Each tooth (235) of second cam teeth (235) comprises generally straight parallel sides (283) and angled sides (284). Parallel sides (283) are operable to engage parallel sides (286) of lock tooth (236) to prevent lock tooth (236) from riding along second cam teeth (235) without assistance from first cam gear (230). This engagement between at least one side (283) and at least one side (286) also prevents cam holding body (276) from rotating about pivot axis (280), thereby preventing end effector (212) from pivoting at articulation joint (211).

Figure 18B:
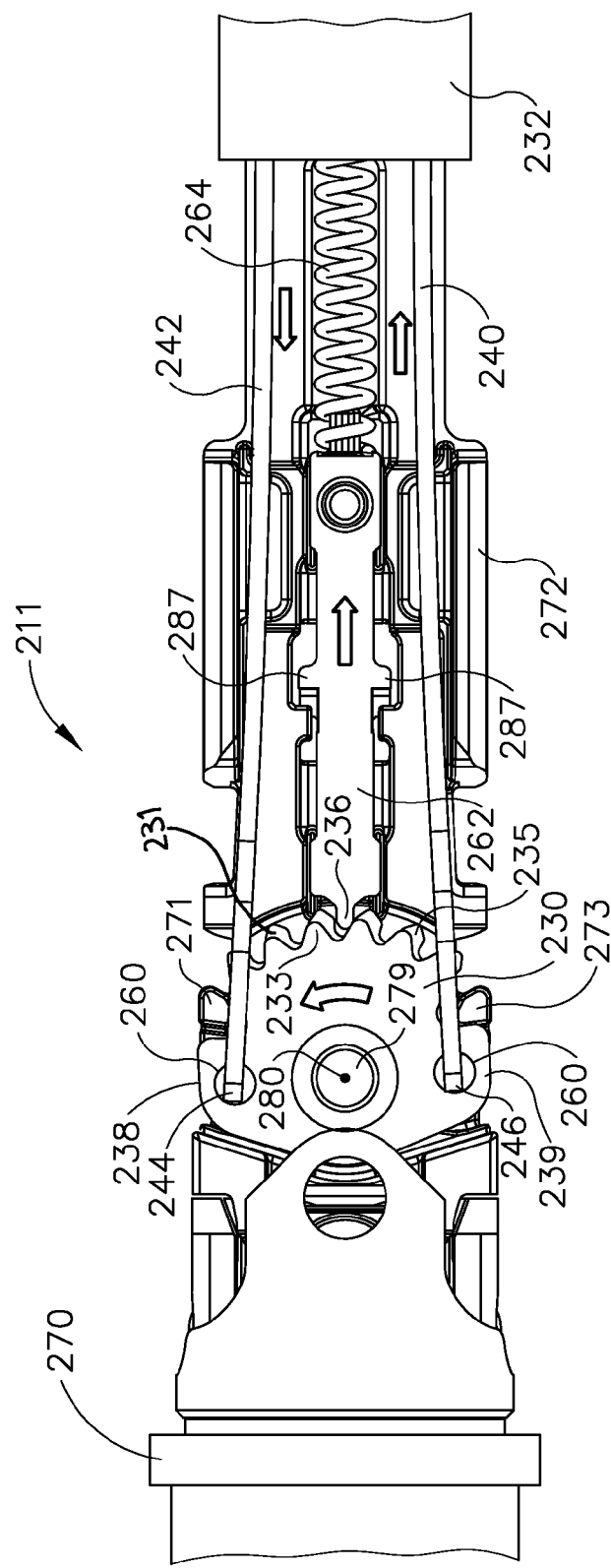
FIG. 18B depicts a top, partially internal view of the articulation joint of the shaft assembly of FIG. 12 with the first and second arms rotating a first cam gear.
Figure 18C:
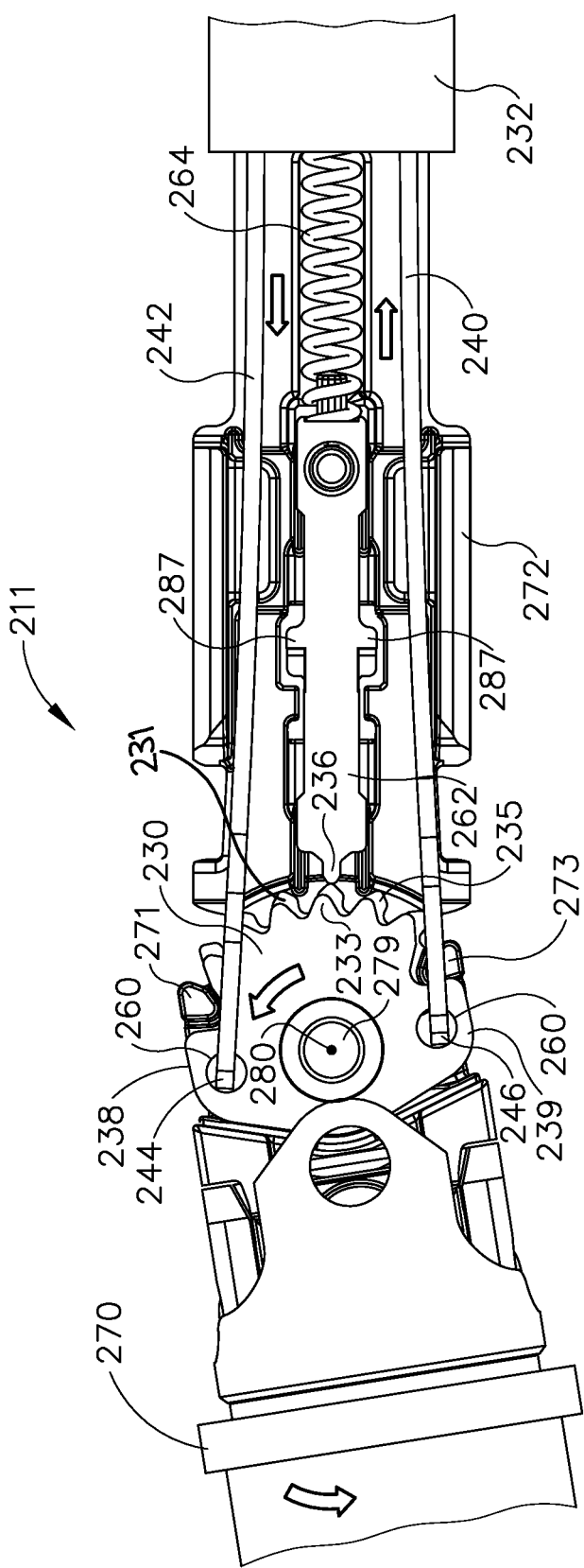
FIG. 18C depicts a top, partially internal view of the articulation joint of the shaft assembly of FIG. 12 with the first and second arms rotating a second cam gear and the first cam gear further.

Once first cam gear (230) rotates as shown in FIGS. 18B-C and as will be described in greater detail below, a rounded triangular tooth (233) of first cam gear (230) will cam against angled sides (281), and will thereby drive lock bar (262) proximally in response to first cam (230) rotating. It should be understood that tooth (233) may have a variety of different shapes other than triangular. Lock tooth (236) moves proximally sufficiently such that angled sides (281) of lock tooth (236) can then eventually engage and ride along angled sides (284) of second cam teeth (235) as first cam gear (230) continues to rotate and as second cam gear (231) rotates. This provides further camming action to drive lock bar (262) proximally. Once lock tooth (236) traverses angled sides (284) of second cam teeth (235), then lock tooth (236) returns distally to a position between the next pair of first cam teeth (233) and second cam teeth (235) similar to the positioning shown in FIG. 19. For illustrative purposes, advancing lock tooth (236) between one set of first cam teeth (233) and second cam teeth (235) to an adjacent set of first cam teeth (233) and second cam teeth (235) may be considered one articulation increment. As lock tooth (236) distally advances, lock tooth (236) strikes second cam gear (231) between second cam teeth (235). It will be understood that lock tooth (236) need not necessarily extend far enough to strike second cam gear (231). For instance, lock tooth (236) may only extend distally such that parallel sides (283) prevent lock tooth (236) from riding along second cam gear (231) without assistance from first cam teeth (233). In the illustrated version, bosses (287) engage joint base (272) to prevent further distal motion of lock bar (262).

As noted above, the operator may wish to pivot end effector (212) at articulation joint (211) to better position end effector (212) in relation to targeted tissue. FIG. 18B shows a second position for articulation joint (211) to move to in response to turning articulation knob (214) shown in FIG. 14. In the illustrated version, the user has turned articulation knob (214) counter clockwise, which rotates articulation pinion (250) counter clockwise as well. As articulation pinion (250) rotates counter clockwise, first rack (252) moves distally and second rack (256) moves proximally in relation to end effector (212). Accordingly, first arm (242) and second arm (240) as shown in FIG. 18B move such that first arm (242) advances toward effector (212) and second arm (240) retracts away from end effector (212). It will be appreciated that the distal portions of first arm (242) and second arm (240) of the illustrated version are not positioned parallel in relation to each other. Instead, first arm (242) and second arm (240) are obliquely angled in relation to each other, though it will be understood that first arm (242) and second arm (240) could be positioned parallel to each other.

Movement of arms (242, 240) as seen in FIG. 18B causes first cam gear (230) to rotate counter clockwise about pivot axis (280). As first cam gear (230) rotates, two actions occur in a generally simultaneous manner. First cam teeth (233) have a rounded triangular shape that urges lock bar (262) proximally away from end effector (212) through a camming action as a result of first cam teeth (233) engaging angled sides (281). Again, teeth (233) may have a variety of different shapes other than triangular. Spring (264) compresses to accommodate proximal motion of lock bar (262). As a result, rounded tip (285) moves proximally sufficient to traverse parallel sides (283). Additionally, cam wings (238, 239) rotate counter clockwise with first cam gear (230). As a result of the rotation, cam wing (239) removes gap (261) between boss (273) and engages boss (273). Meanwhile, cam wing (238) moves rotationally away from boss (271). It will be understood that while first cam gear (230) and lock bar (262) have moved in response to the movement of arms (242, 240) during the transition from the configuration shown in FIG. 18A to the configuration shown in FIG. 18B, second cam gear (231) and accordingly end effector (212) have not yet moved. Thus, end effector (212) remains in a straight orientation at this stage.

FIG. 18C shows a third position of articulation joint (211). It will be understood that the user continues to rotate articulation knob (214) in an effort to articulate end effector (212). Arms (242, 240) continue to move such that first arm (242) moves distally and second arm (240) moves proximally. Movement of arms (242, 240) continues to rotate first cam gear (230), which causes cam wing (239) to rotationally move further thereby urging boss (273) to rotationally move as well. Since boss (273) is unitary with second cam gear (231), second cam gear (231) begins to rotate. As second cam gear rotates (231), lock bar (262) moves further proximally as a result of angled sides (284) camming against angled sides (281) of lock tooth (236). Thus, lock tooth (236) rides along second cam teeth (235). Second cam gear (231) rotates until tip (288) of second cam gear (231) engages rounded tip (285). Second cam teeth (235) have parallel sides (283) such that angled edges (281) of lock tooth (236) can engage angled sides (284) only after first cam teeth (233) urges lock tooth (236) proximally such that rounded tip (285) traverses parallel sides (283). Prior to riding along first cam teeth (233), lock tooth (236) is generally unable to ride along second cam teeth (235) due to parallel sides (283) engaging parallel sides (286). It will further be appreciated that as lock tooth (236) rides along angled sides (284), lock tooth (236) disengages first cam teeth (233). As also seen in FIG. 18C, lock bar (262) and lock tooth (236) have moved to a proximal most position with just second cam teeth tip (288) being in contact with lock tooth (236). Also as a result of rotation of second cam gear (231), cam holding body (276) and accordingly, sleeve (270), which leads to end effector (212), articulates in a counter clockwise direction.

Figure 18D:
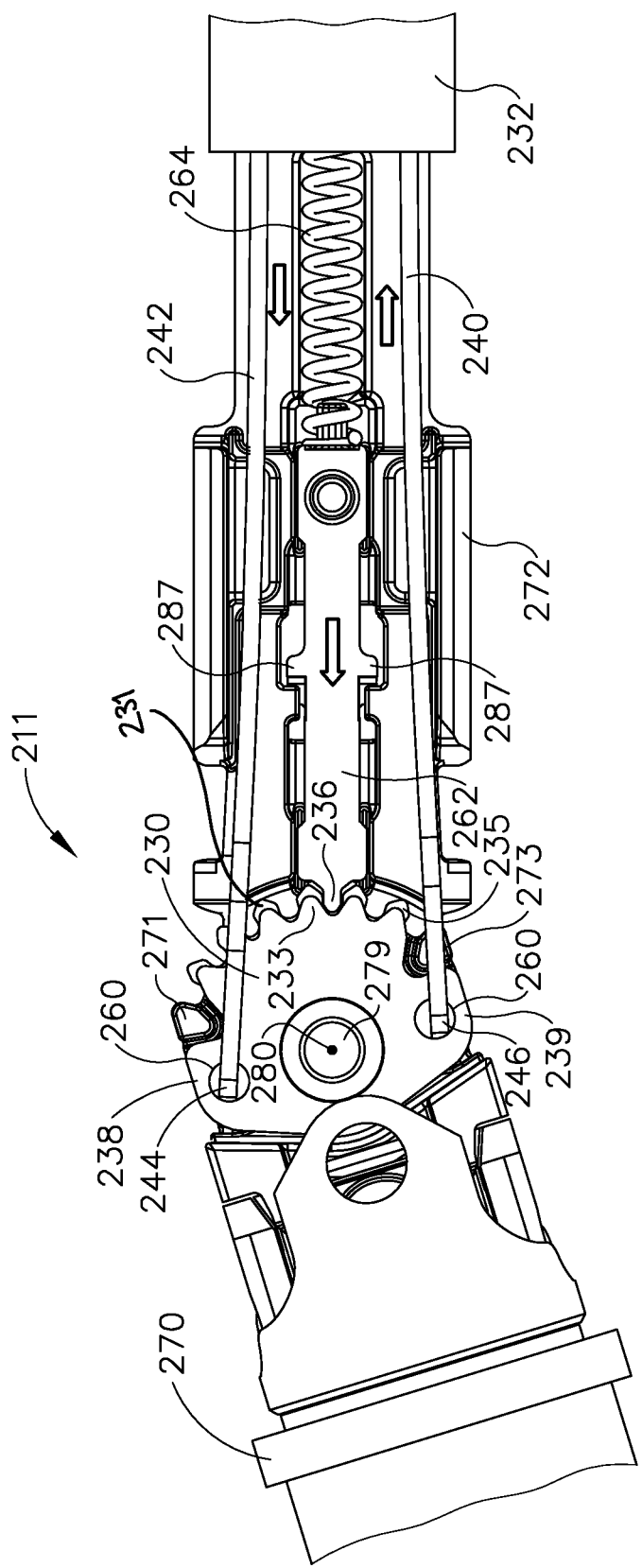
FIG. 18D depicts a top, partially internal view of the articulation joint of the shaft assembly of FIG. 12 with a lock bar resiliently positioning a lock tooth between teeth of the first cam gear and the second cam gear.

FIG. 18D shows a fourth position for articulation region (211). Once again, it will be understood that user is continuing to rotate articulation knob (214) in an effort to cause further articulation of end effector (212). Arms (242, 240) continue to move such that first arm (242) moves distally further and second arm (240) moves proximally further. Movement of arms (242, 240) continues to rotate first cam gear (230), which causes cam wing (239) to push boss (273) rotationally further. Lock tooth (236) continues to ride along second cam teeth (235) until the distal bias caused by spring (264) urges lock bar (262) into the position shown in FIG. 18D. It will be appreciated that when lock bar (262) snaps into the position shown in FIG. 18D, an audible click or snap may be heard or felt. As a result, the user receives audible and/or tactile confirmation that lock tooth (236) has moved from between one set of cam teeth (233, 235) to another or otherwise has rotated by a single articulation increment. When in the position shown in FIG. 18D, first cam gear (230) stops rotating and lock tooth (236) fits between cam teeth (233, 235). Sleeve (270) and accordingly end effector (212) stop articulating. A positive lock has formed because any rotational motion of second cam gear (231) urged by transverse forces on end effector (212) would result in parallel sides (286) engaging parallel sides (283) and stopping any further rotation of second cam gear (231), which locks the articulation of end effector (212). It should be understood that the transition from the configuration shown in FIG. 18A to the configuration shown in FIG. 18D represents articulation through one articulation increment, or increment of articulation motion, in which the distance is defined generally by the spaces between second cam teeth (235)

It will be understood that in the position shown in FIG. 18D, end effector (212) has articulated thereby providing the user with a shaft assembly (200) with an articulated end effector (212). It will be appreciated that the user may wish to use shaft assembly (200) in the position shown in FIG. 18D or may wish to pivot end effector (212) further by one or more additional articulation increments. In the event that the user does not rotate articulation knob (214) further, the locking of lock tooth (236) between first cam teeth (233) and second cam teeth (235) prevents end effector (212) from pivoting to return to a straight position. Once end effector (212) has been articulated to a desired angle (a), it will be understood that the user may actuate firing beam (213) to drive knife (248) to cut and drive staples through tissue. For instance, knife (248) and firing beam (213) may be in communication through, for instance, a bendable beam such that firing beam (213) can advance through any degree of pivot of articulation joint (211).

Figure 18E:
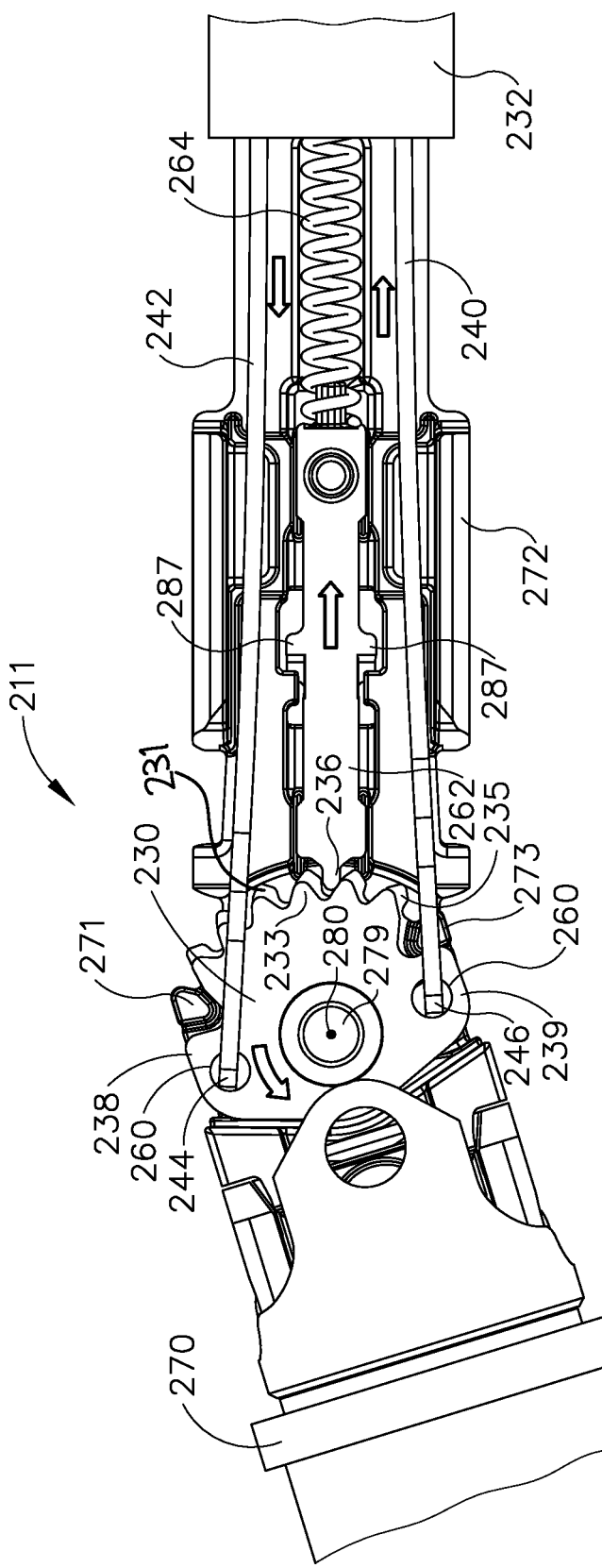
FIG. 18E depicts a top, partially internal view of the articulation joint of the shaft assembly of FIG. 12 with the first and second arms rotating the first cam gear yet even further.

FIG. 18E shows a fifth position for articulation joint (211) in the event that the user wishes to pivot end effector (212) further. Once again, it will be understood that user continues to rotate articulation knob (214). As a result, arms (242, 240) continue to move such that first arm (242) moves distally further and second arm (240) moves proximally further. Movement of arms (242, 240) continues to rotate first cam gear (230), which causes cam wing (239) to push boss (273) rotationally. First cam gear (230) and second cam gear (231) move similarly as shown in FIGS. 18B-D, which causes end effector (212) to articulate further as well as lock in a more articulated position. It will be understood that the user may continue to rotate articulation knob (214) to cause end effector (212) to pivot as far as the user desires. Furthermore, the user may rotate articulation knob (214) in the opposite direction to cause arms (242, 240) and cam gears (230, 231) to move in the opposite direction, thereby causing end effector (212) to articulate in an opposite direction.

As seen in the exemplary actuation shown in FIGS. 18A-18E, first cam gear (230) is operable to unlock articulation joint (211) and pivot end effector (212) at articulation joint (211) about pivot axis (280), by transferring motion from arms (242, 240) to first cam gear (230). In addition, second cam gear (231) and lock bar (262) cooperate to lock articulation joint (211), to thereby lock the angle (a) of end effector (212) relative to the longitudinal axis (LA) of shaft assembly (200).

V. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013 (now U.S. Pat. No. 8,844,789, issued Sep. 30, 2014), the disclosure of which is incorporated by reference herein; U.S. Pub. No. 2012/0199630, entitled "Robotically-Controlled Surgical Instrument with Force-Feedback Capabilities," published Aug. 9, 2012 (now U.S. Pat. No. 8,820,605, issued Sep. 2, 2014), the disclosure of which is incorporated by reference herein; U.S. Pub. No. 2012/0132450, entitled "Shiftable Drive Interface for Robotically-Controlled Surgical Tool," published May 31, 2012 (now U.S. Pat. No. 8,616,431, issued Dec. 31, 2013), the disclosure of which is incorporated by reference herein; U.S. Pub. No. 2012/0199633, entitled "Surgical Stapling Instruments with Cam-Driven Staple Deployment Arrangements," published Aug. 9, 2012 (now U.S. Pat. No. 8,573,461, issued Nov. 5, 2013), the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012 (now U.S. Pat. No. 8,602,288, issued Dec. 10, 2013), the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued Apr. 5, 2016, the disclosure of which is incorporated by reference herein; U.S. Pub. No. 2012/0203247, entitled "Robotically-Controlled Surgical End Effector System," published Aug. 9, 2012 (now U.S. Pat. No. 8,783,541, issued Jul. 22, 2014), the disclosure of which is incorporated by reference herein; U.S. Pub. No. 2012/0211546, entitled "Drive Interface for Operably Coupling a Manipulatable Surgical Tool to a Robot," published Aug. 23, 2012 (now U.S. Pat. No. 8,479,969, issued Jul. 9, 2013); U.S. Pub. No. 2012/0138660, entitled "Robotically-Controlled Cable-Based Surgical End Effectors," published Jun. 7, 2012 (now U.S. Pat. No. 8,800,838, issued Aug. 12, 2014), the disclosure of which is incorporated by reference herein; and/or U.S. Pub. No. 2012/0205421, entitled "Robotically-Controlled Surgical End Effector System with Rotary Actuated Closure Systems," published Aug. 16, 2012 (now U.S. Pat. No. 8,573,465, issued Nov. 5, 2013), the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   (a) a body; and
   (b) a shaft assembly in communication with the body; wherein the shaft assembly comprises:
      (i) an end effector having an articulation joint;
      (ii) a first cam gear rotatably positioned within the shaft assembly,
      (iii) a second cam gear in communication with the end effector at the articulation joint, and
      (iv) a lock bar distally biased to lock against the second cam gear, wherein the first cam gear is rotatable through a first range of motion to unlock the lock bar relative to the second cam gear, wherein the first cam gear is rotatable through a second range of motion to rotate the end effector at the articulation joint, wherein the lock bar comprises a lock tooth, wherein the second cam gear comprises second cam teeth, wherein the lock bar is shaped to complement the shape of the second cam teeth.

2. The apparatus of claim 1, wherein the first cam gear comprises a plurality of cam wings configured to urge rotation of the second cam gear.

3. The apparatus of claim 2, wherein the second cam gear comprises a plurality of bosses configured to engage the plurality of cam wings.

4. The apparatus of claim 1, further comprising an articulation knob in communication with a first arm and a second arm, wherein the first arm and the second arm are in opposing communication with the first cam gear, wherein the articulation knob is configured to rotate to effectuate opposing motion of the first arm and the second arm.

5. The apparatus of claim 1, wherein the second cam teeth comprise straight walls.

6. The apparatus of claim 1, wherein the first cam gear comprises first cam teeth, wherein the first cam teeth have a rounded shape.

7. The apparatus of claim 1, wherein the first cam gear comprises first cam teeth, wherein the second cam gear comprises second cam teeth, wherein the lock tooth is positionable between the first cam teeth and the second cam teeth.

8. The apparatus of claim 7, wherein the lock tooth is configured to snap into a position between the first cam teeth and the second cam teeth, wherein the lock tooth is operable to produce an audible click when the lock tooth snaps into the position between the first cam teeth and the second cam teeth.

9. The apparatus of claim 7, wherein the lock tooth is configured to snap into a position between the first cam teeth and the second cam teeth, wherein the lock tooth is operable to produce a tactile feedback click when the lock tooth snaps into the position between the first cam teeth and the second cam teeth.

10. The apparatus of claim 1, wherein the first cam gear comprises cam wings, wherein the second cam gear comprises bosses, wherein the cam wings and the bosses are positionable such that a gap is maintained between the cam wings and the bosses.

11. The apparatus of claim 1, wherein the first cam gear and the second cam gear are coaxially aligned with a pivot axis, wherein the pivot axis is perpendicular to the end effector.

12. The apparatus of claim 1, wherein the second cam gear comprises second cam teeth having parallel sides, wherein the lock bar comprises a lock tooth having parallel sides, wherein the parallel sides of the lock tooth are configured to engage the parallel sides of the second cam teeth to thereby prevent rotation of the second cam gear.

13. The apparatus of claim 1, wherein the lock bar comprises at least one laterally extending boss configured to prevent the distal movement of the lock bar beyond a predetermined point.

14. The apparatus of claim 1, further comprising a spring in communication with the lock bar, wherein the spring is operable to distally bias the lock bar.

* * * * *